(12) United States Patent
Coates et al.

(10) Patent No.: US 6,452,179 B1
(45) Date of Patent: Sep. 17, 2002

(54) ON-SITE ANALYZER

(75) Inventors: John Coates, Newton, CT (US); Neil Rosenbaum, Atlanta; Yosef Abuneaj, Tucker, both of GA (US)

(73) Assignee: Global Technovations, Inc., Palm Beach Gardens, FL (US)

( * ) Notice: Subject to any disclaimer, the term of this patent is extended or adjusted under 35 U.S.C. 154(b) by 0 days.

(21) Appl. No.: 09/372,968

(22) Filed: Aug. 12, 1999

Related U.S. Application Data

(60) Provisional application No. 60/096,494, filed on Aug. 14, 1998.

(51) Int. Cl.[7] .................................................. G01J 3/30
(52) U.S. Cl. .................................. 250/339.09; 356/313
(58) Field of Search ..................... 250/339.09, 338.1; 356/307, 313; 702/8

(56) References Cited

U.S. PATENT DOCUMENTS

| | | | |
|---|---|---|---|
| 3,729,259 A | * 4/1973 | Cooper et al. | 356/307 |
| 4,618,769 A | 10/1986 | Johnson et al. | 250/338 |
| 5,194,910 A | 3/1993 | Kirkpatrick, Jr. et al. | 356/70 |
| 5,285,251 A | 2/1994 | Pilloud et al. | |
| 5,303,165 A | 4/1994 | Ganz et al. | 364/571.01 |
| 5,347,475 A | 9/1994 | Taylor et al. | 364/571.01 |
| 5,428,558 A | 6/1995 | Cahill et al. | 364/571.02 |
| 5,517,427 A | 5/1996 | Joyce | 364/510 |
| 5,521,698 A | 5/1996 | Carroll et al. | 356/70 |
| 5,537,336 A | 7/1996 | Joyce | 364/510 |
| 5,610,706 A | 3/1997 | Carroll et al. | 356/70 |
| 5,734,587 A | 3/1998 | Backhaus et al. | |
| 5,757,482 A | 5/1998 | Fuchs et al. | |

OTHER PUBLICATIONS

"Calibrating the Wavelength of Your Spectrometer", Ocean Optics, Inc., Jul. 29, 1998.
"Conversion of a Sequential Inductively Coupled Plasma Emission Spectrometer into a Multichannel Simultaneous System Using a Photodiode Array Detector", Journal of Automatic Chemistry V.20 N.3 (1998) pp 69–75.
"Simultaneous Multielemental Determination Using a Low–Resolution Inductively Coupled Plasma Spectrometer/Diode Array Detection System", Maria F. Pimentel, et al., Spectrochimica Acta Part B 1997, pp 2151–61.

* cited by examiner

Primary Examiner—Georgia Epps
Assistant Examiner—Richard Hanig
(74) Attorney, Agent, or Firm—David Aker

(57) ABSTRACT

An apparatus (10) for analyzing lubricant oils and functional fluids includes an optical emission spectrometer (OES) (26) having a substantially continuously valued wavelength versus intensity output (140). The OES (26) analyzes light captured from a spark emission stand (58) through which the fluid sample is flowed. An expert system (160–172) operates according to a set of Rules that corrects background influence from the electrodes, and generates diagnostic text (174) for an operator based on the information about the fluid sample provided by the OES (26) and other measurement devices. The apparatus (10) is reduce in size, weight and cost.

20 Claims, 15 Drawing Sheets

FIG. 17

Acme Trucking Company
3213 Brewster Street
Atlanta, GA 30340
404-555-3654

Unit Make: Dodge
Unit Model: Dakota
Oil Capacity: 5.0 Quarts

Engine Size:

Unit ID: C68
Test Date/Time: 05/14/1998 00:00
Equipment: GS

| Sample Data on 05/14/1998 | Wear Metals (in Parts per Million) | | | | | | | | | | Physical Properties | | | | | | |
|---|---|---|---|---|---|---|---|---|---|---|---|---|---|---|---|---|---|
| | Aluminum | Chromium | Copper | Iron | Lead | Tin | Silicon | Potassium | Sodium | | Water | Oxidation | Visc @ 100 | Glycol | Fuel | Nitration | SAE |
| ID: 000445 | 21 | 0 | 82 | 203 | 0 | 48 HN | 47 | 182 A | 1 | | 0.0 | 0.4 | 12.0 | 0.0 | 0.0 | 1.5 | 39 |
| Oil Brand: Pennzoil | | | | | | | | | | | | | | | | | |
| Oil Type: Heavy Duty | | | | | | | | | | | | | | | | | |
| Oil Weight: 10W30 | | | | | | | | | | | | | | | | | |
| Time On Unit: 78000 M | | | | | | | | | | | | | | | | | |
| Time On Oil: 4300 M | | | | | | | | | | | | | | | | | |

* Wear is in the high normal range. To further improve your engine condition it is advisable to have a strict adherence to the maintenance practices prescribed in your manual and reduce your oil change interval. Evidence of water treatment chemicals present, but below detection limits of glycol. Check for source of coolant leak. Drain oil and change filter if not already done. Resample next service interval to further monitor.

* Assuming normal oil consumption and based on provided information, wear metal evaluation varies per make and model. Total Miles/Hours and the Miles/Hours the oil has been in service.
LN = Low Normal    HN = High Normal    N/A = Non Applicable    A = Abnormal    E = Excessive

174

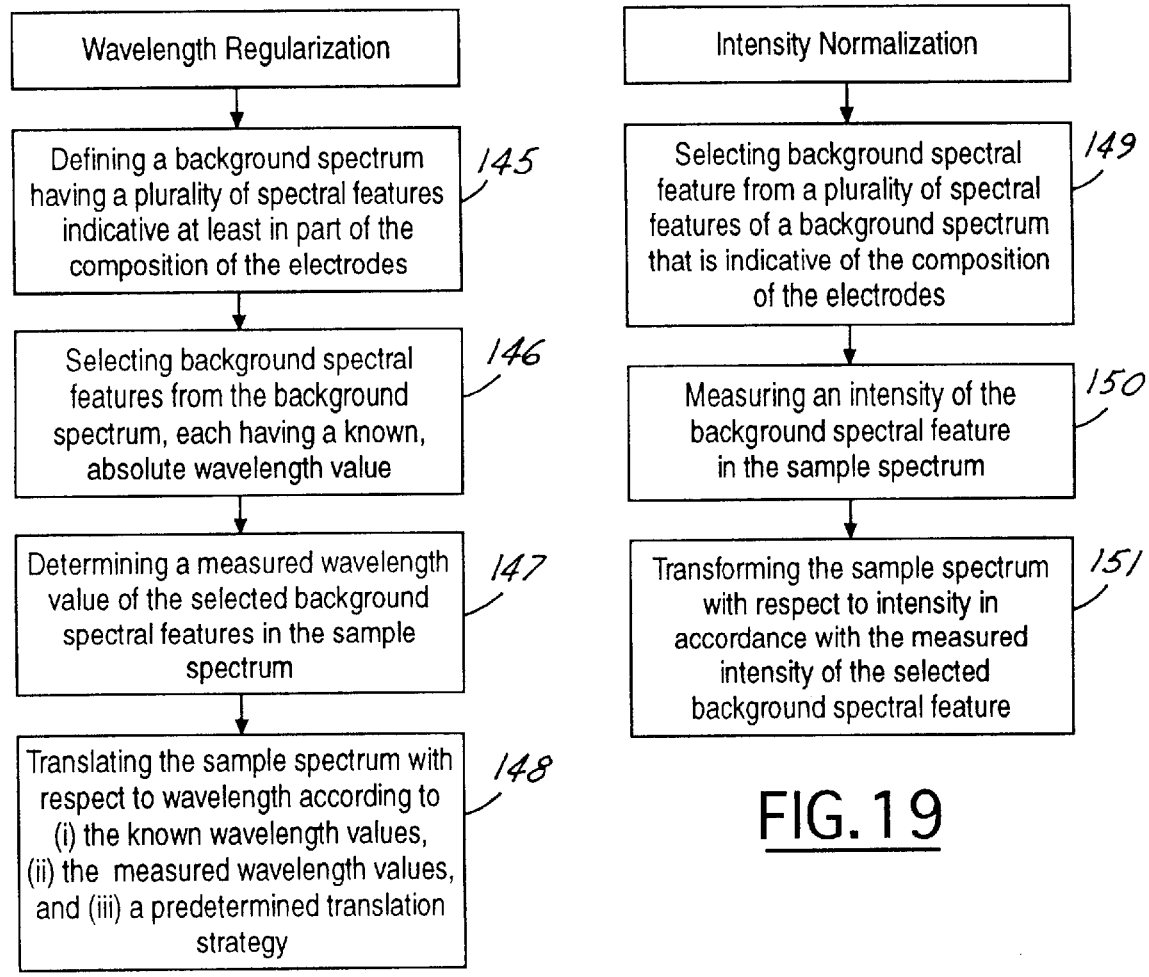

ON-SITE ANALYZER

CROSS-REFERENCES TO RELATED APPLICATIONS

This application claims the benefit of U.S. provisional patent application serial No. 60/096,494 filed Aug. 14, 1998 which is hereby expressly incorporated herein by reference in its entirety.

BACKGROUND OF THE INVENTION

1. Technical Field

This invention relates generally to an apparatus and method for analyzing a fluid sample, and, more particularly, to a self-contained analyzer for on-site use and analysis.

2. Discussion of the Related Art

There has been much interest and investigation into apparatus and methods for obtaining accurate analysis of lubricating oils (used and fresh) as well as functional fluids. The term "functional fluids" relates to liquid materials used in mechanical equipment, and which may be or may perform primarily lubrication and/or power transmission functions (e.g., gearbox oils, automatic transmission fluid, machine oils and hydraulic fluids or oils, etc.). "Functional fluids" also includes coolants, thermal transmission media, and fuels. The reasons for such interest include, but are not limited to, (i) the assessment of the constituent, condition and quality of the oil/fluid, (ii) the condition of the equipment from which the oil/fluid was drawn, and (iii) the condition of components of such equipment.

As is known, oil is generally used to lubricate moving parts in mechanical systems, such as engines, transmissions, hydraulics and vehicles. Certain substances, referred to generally as contaminants, are not originally present in the oil but rather are produced as the by-products of wear and corrosion. For example, metal particulates may be formed through abrasion or chemical corrosion and cause further deterioration of internal parts. In addition, normal operation causes oxidation, nitration and sulfation of the oil, altering a desired chemistry thereof. Further, leaks between the cooling systems and the lubricating system may cause coolant (mixtures of water, ethylene glycol and other coolant chemicals) to be introduced into the oil.

Lubricant oil filters are designed to remove the larger size particulates from oil. However, this gross filtering nonetheless leaves the majority of smaller contaminants free to further affect the equipment. For example, non-metallic components, such as pump diaphragms, gaskets and seals, fluid lines and the like, may be further affected. Moreover, contaminants in the oil, such as ethylene glycol, fuel, silicone, water, soot and other chemicals may also present concerns.

Historically, accurate oil analysis has been provided mainly in a laboratory setting, such as, for example, a system utilized in a laboratory as disclosed in U.S. Pat. No. 3,526,127 issued to Sarkis on Sep. 1, 1970.

One approach to accurate on-site oil analysis was to provide a self-contained test assembly in a single housing, as described in U.S. Pat. Nos. 5,517,427 and 5,537,336, both issued to Joyce (the "Joyce patents"), both hereby expressly incorporated by reference in its entirety. The Joyce patents disclose a test assembly that includes an infrared (IR) spectrometer and an optical emission spectrometer for producing a report on the amount of certain metals in an oil sample, other oil contaminants such as water, glycol, soot, etc. as well as oil condition. With respect to the optical emission spectrometer portion, the Joyce patents disclose the use of "photocells" (the commercial embodiment corresponding to the Joyce patents employed well-known photo multiplier tubes (PMT)) to optically monitor spark induced light emissions of the oil sample to determine wear metals content.

Although PMTs in the manner configured (i.e., incorporated into a large monochromator in the commercial embodiment corresponding to the Joyce patents) provide "high resolution", such a configurations presents certain constraints. First, inherent in such systems are certain geometric and mechanical constraints imposed by the physical dimensions of a PMT. Since each PMT was configured to monitor a fixed wavelength, the system had to be made relatively, physically large to ensure that light from multiple wavelengths would not impinge on the same PMT. Second, the configuration provided little if any flexibility in emission line selection/reconfiguration. Finally, as the number of monitored emission lines increased, so would the corresponding cost (due to the required addition of another PMT). Thus, while the apparatus disclosed in the Joyce patents provided satisfactory performance, it would be desirable to provide an apparatus having a reduced size, weight and cost.

Accordingly, there is a need to provide an improved apparatus for analysis of a fluid sample that minimizes or eliminates one or more of the problems as set forth above.

SUMMARY OF THE INVENTION

One object of the present invention is to provide an apparatus for analyzing a fluid sample having a reduced size, weight and cost.

It is a further object to provide such an apparatus configurable for analyzing and characterizing liquid lubricants as well as functional fluids (e.g., hydraulic oils, etc.).

It is yet a further object of the present invention to provide such an apparatus that is highly customizable, and which can be reconfigured to detect and analyze desired, alternate elements.

To achieve these and other objectives, according to one aspect of the present invention, an apparatus for analyzing a fluid sample to determine constituents thereof is provided. The apparatus includes five (5) major parts: a housing, a fluid transfer assembly, an infrared (IR) spectrometer assembly, an optical emission spectrometer (OES) assembly, and a computer controller.

The fluid transfer assembly includes an inlet configured to receive the fluid sample and is configured to selectively flow the fluid sample to an outlet thereof. The IR spectrometer assembly is disposed in the housing, coupled to the outlet, and is configured to analyze the fluid sample and generate a first data set. In a constructed embodiment, the IR spectrometer comprises a Fourier Transform Infrared (FTIR) spectrometer. The OES assembly is also disposed in the housing, coupled to the outlet, and is configured to analyze the fluid sample and generate a second data set. The second data set is substantially continuously valued over a first predetermined wavelength range. Finally, the computer controller is connected to the transfer assembly, the IR spectrometer assembly, and the OES assembly and is configured to control the operation of the apparatus in accordance with a predetermined operating strategy. The computer controller is further configured to determine constituents of the fluid sample in accordance with the first and second data sets.

In a preferred embodiment, the OES assembly includes a fluid sample excitation assembly, such as a spark emission assembly that includes electrodes. The spark assembly is configured to excite the fluid sample to spectroemissive levels to thereby generate radiation characteristic of the constituents in the fluid sample. The OES assembly further includes a first spectrometer configured to receive the radiation and generate a first spectral pattern, and a second spectrometer configured to receive the radiation and generate a second spectral pattern. Also in the preferred embodiment, the first spectrometer has a first resolution, and the second spectrometer has a second resolution less than the first resolution, which preferably may be 0.3 nm (half-width at half-height), and 1.0 nm (half-width at half-height), respectively.

In another aspect of the invention, the IR spectral analyzer assembly is configured to include an inventive flow cell assembly which minimizes the undesirable effects of fringing. "Fringing" is manifested as a sinusoidal feature in the intensity-versus-wavelength final spectrum, which interferes with the measurement of oil constituents. The IR spectral analyzer assembly includes an IR source, the flow cell assembly, and a detector assembly. The IR source is configured to generate an IR radiation beam focused along a principal axis to converge at the detector. The detector assembly is spaced apart from the IR source. The flow cell assembly includes a sample cell and a compensator window, and is slidably movable along a motion axis transverse to the principal axis. The flow cell assembly moves between a first position wherein the compensator window is optically intermediate the IR source and the detector, and a second position wherein the sample cell is optically intermediate the IR source and the detector.

The compensator window and the sample cell are each arranged such that a respective normal axis associated therewith define a predetermined tilt angle, preferably between about 20–25 degrees relative to the principal axis. Moreover, in a preferred embodiment, the compensator window and the sample cell each have an effective thickness and index of refraction that are substantially equal. The foregoing insures that the focused images of the sample (i.e., through the sample cell), and the background (i.e., through the compensator window) coincide on the detector.

In yet another aspect of the present invention, a method is provided for adjusting the wavelength axis of a sample spectrum of a fluid sample generated by a spectrometer having a pair of electrodes.

The foregoing permits the use of low resolution optical emission spectrometers to identify and quantitate elements, contaminants, and additives of interest in fluid samples.

BRIEF DESCRIPTION OF THE DRAWINGS

Other features, advantages, and uses of the present invention will be readily appreciated by one of ordinary skill in the art by reference to the following detailed description when considered in connection with the accompanying drawings, a brief description of which is set forth immediately hereinafter.

FIG. 17 shows a sample output report generated by the apparatus of FIG. 1;

FIG. 18 is a flowchart diagram of a method of regularizing a sample spectrum; and, FIG. 19 is a flowchart diagram of a method of normalizing an intensity of a sample spectrum.

DETAILED DESCRIPTION OF THE PREFERRED EMBODIMENTS

Figure 1:
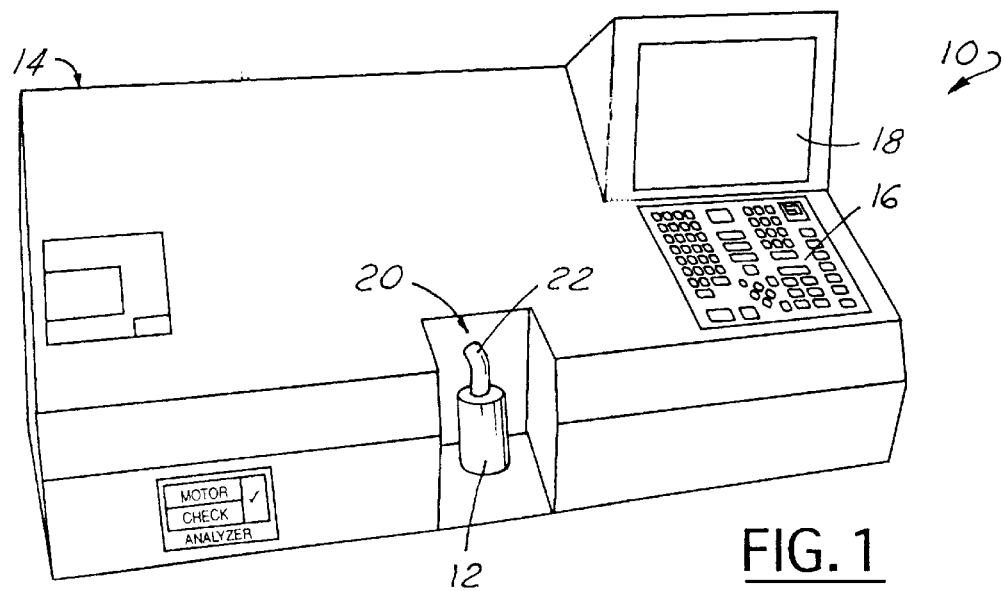
FIG. 1 is a perspective view of an apparatus for analyzing a fluid sample in accordance with the present invention.

Referring now to the drawings wherein like reference numerals are used to identify identical components in the various views, FIG. 1 shows, in perspective form, an apparatus 10 for analyzing a fluid sample 12 to determine constituents thereof. "Constituents" may refer to (i) additives introduced into the fluid by design, (ii) wear metals (such as aluminum, chromium, copper, iron, lead, and tin), and (iii) contaminants and fluid condition/degradation, which should be understood to includes not only unexpected or undesired substances, but also changes in the fluid resulting from aging, usage, leakage of fluid from elsewhere into the fluid sample, and the like (e.g., $H_2O$, glycol, fuel, soot, oxidation, nitration, sulfation, estimated viscosity, Total Base Number (TBN), and the like). Additionally, an extended set of detectable elements may include: Ag, Al, B, Ba, Ca, Cd, Cr, Cu, Fe, K, Mg, Mn, Mo, Na, Ni, P, Pb, Si, Sn, Ti, V, and Zn. Note that detection of Ag may require a changes in the electrode set when the electrodes used are silver, as in a constructed embodiment.

Apparatus 10 is particularly suited for on-site measurement of used and fresh lubricating oils (e.g., motor oils) and functional fluids for the assessment of equipment condition and lubricant (functional fluid condition and quality). The term "equipment" herein may relate to internal combustion engines (two-cycle and four-cycle, diesel, gasoline or natural gas fired, or an alternate fuel-propelled engine), transmissions (manual and automatic), gearboxes, rear axles and differentials, turbines, and/or any other piece of rotating and/or reciprocating component which may be lubricated by a minimal or partial-loss lubricant system.

While, in a preferred embodiment, apparatus 10 is specifically adapted for automotive applications, apparatus 10 may easily be adapted so as to extend to any powered lubrication system, including industrial, off-highway, stationary, locomotive, marine, aviation, miliary, and power generation systems.

Moreover, while, in a preferred embodiment, apparatus 10 is illustrated and described for analyzing used lubricating oils, apparatus 10 may be extended for use in the characterization and quality assessment of fresh, unused oil products (i.e., may be used for production control applications, such as at a refinery site).

An apparatus in accordance with the present invention provides an automated, integrated apparatus for the measurement of oil/lubricant condition, including the presence of key contaminants, as well as the assessment of equipment (and components thereof) from which the fluid sample 12 was drawn. The apparatus provides diagnostic information (exemplary report shown in FIG. 17) from an expert system portion thereof, based on operator-input data, measured sample data, and predetermined data, for many equipment types. Two main technologies are included to determine sample constituent analysis: (i) optical emission spectroscopy technology, and (ii) infrared (IR) spectroscopy technology. In one embodiment, certain standard analyses, such as viscosity, are determined indirectly based on a known spectral response for various standard oil and contamination. In alternate embodiments, where more accurate viscosity measurements are desirable, the apparatus may include a viscometer.

Figure 2:
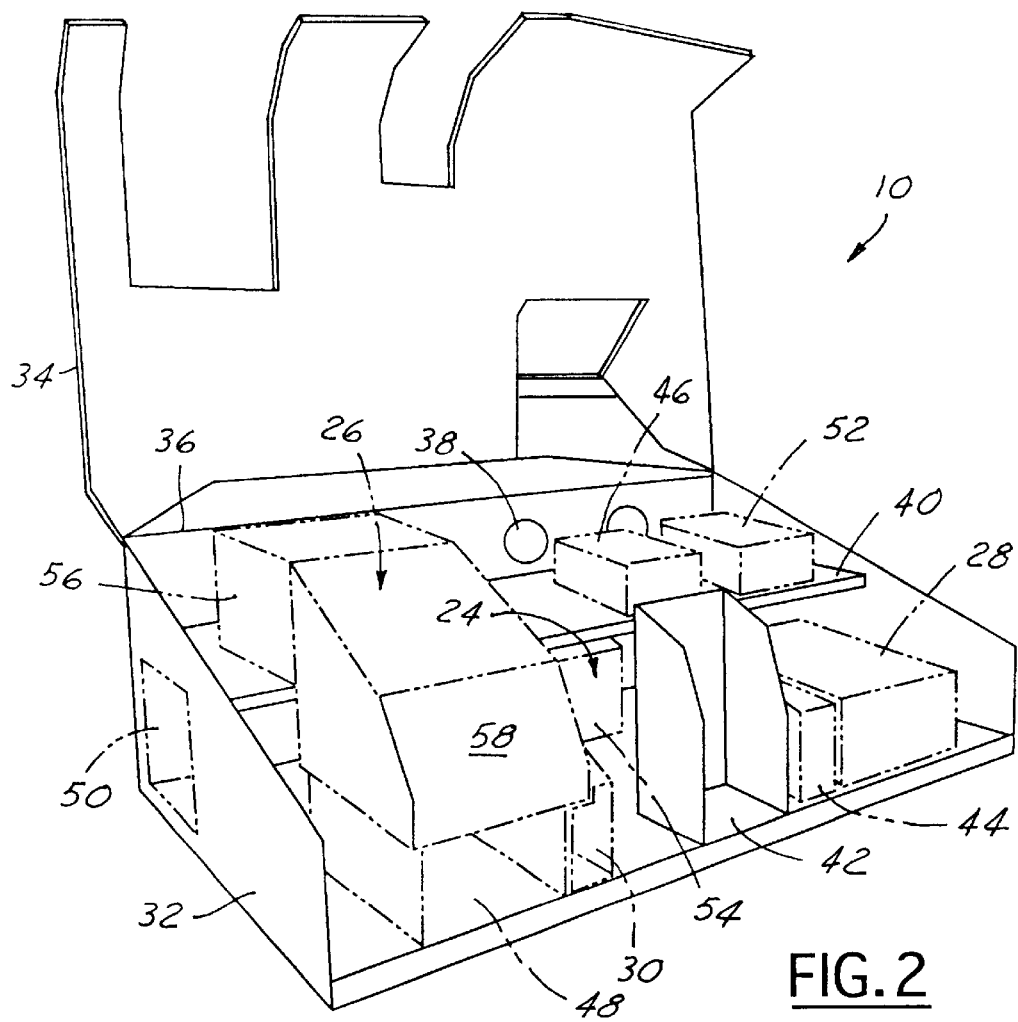
FIG. 2 is a perspective view of the apparatus shown in FIG. 1 having a housing portion in an open position.

Referring to FIGS. 1 and 2, apparatus 10 includes a 2-tier "clam-shell" housing 14, an integrated keypad 16, a display 18, and an integrated fluid transfer assembly 20 having a sipper inlet 22, an infrared (IR) spectral analyzer system, such as Fourier Transform Infrared (FTIR) spectrometer system 24, a low resolution optical emission spectrometer (OES) assembly 26, a computer controller 28, and, optionally, a viscometer 30 and/or similar measuring apparatus like a densitometer. FIG. 1 shows housing 14 in a closed position. In a constructed embodiment, apparatus 10 may be about 965 mm (38 inches) Wide by 559 mm (22 inches) in Depth by 432 mm (17 inches) in Height (521 mm (20.5 inches) in Height at display). In such a constructed embodiment, apparatus 10 may weigh about 67 Kg (150 lbs.).

FIG. 2 shows a "bench-top" embodiment of apparatus 10 with housing 14 in an open position. In an alternate embodiment, apparatus 10 may take the form of a stand alone embodiment on a movable custom-designed cart (not shown). Further alternate embodiments contemplated include a rack-mounted embodiment, an environmentally protected embodiment (NEMA enclosure), and a transportable/portable embodiment. The ability to change the form of apparatus 10 flows from the modularity of the hardware and software. In contrast, in previous (high resolution) analyzers employing photo multiplier tubes (PMTs) and large monochromators were constrained by geometrical considerations.

FIG. 2 illustrates the modular approach to hardware configuration and other mechanical features of apparatus 10. Housing 14 includes a base portion 32, an upper portion 34, a pivot 36, a rear access panel/opening 38, and a shelf 40. An inner bottom surface of base portion 32 provides a first, lower tier, while shelf 40 provides a second, upper tier. In the open position (as illustrated in FIG. 2), housing 14 provides easy access to many of the functional components. Many of the power supplies are disposed on shelf 40, adjacent a plurality of heat extraction fans (not shown), thereby providing rapid removal of heat generated by the supplies. Further, housing 14 has been engineered to help comply with CE requirements—minimal radiation and emissions, plus immunity to external electrical or radiative interference. The ease of access to the internal location of apparatus 10, when housing 14 is in the open position, eases assembly of apparatus 10. In addition, all removable surfaces and covers are protected by interlocks, preventing exposure to high voltage components (i.e., the main line voltage is disconnected when the interlocks are activated).

Housing 14 further includes means (not shown) for isolating apparatus 10 from external vibrations, especially for the optical components. In a constructed embodiment, four (one of which includes height adjustment) shock-absorbing feet are provided to define a first level of vibration isolation. Apparatus 10 further includes a second level of vibration isolation, namely, direct shock-mounts on the individual optical components (not shown).

Fluid transfer assembly 20 is provided for receiving a fluid sample 12 at inlet 22 (FIG. 1), and flowing the sample concurrently, under control of computer controller 28, to the various measurement instruments in apparatus 10. Transfer assembly 20 comprises a sampling region 42, one or more sample distribution components designated generally at phantom-line box 44, a sample distribution power supply 46, a waste receptacle region 48, and a flushing medium (fluid) reservoir 50. Waste receptacle region 48 is adapted in size and configuration to receive a waste tray (not shown) to receive analyzed oil/fluid from apparatus 10. A level sensor is further provided (not shown) to alert an operator of apparatus 10 when the waste tray needs to be emptied.

The fluid used for flushing apparatus 10 may comprise conventional and well-known materials, and may comprise thin hydrocarbon material. In a constructive embodiment, a citrus-based product, commercially available under the brand name "ELECTRON", was satisfactorily used, available from Ecolink, Inc., a subsidiary of Sentry Chemical Company, Stone Mountain, Ga.

In the illustrative embodiment, FTIR spectrometer system 24 includes, from a packaging viewpoint, a FTIR power supply 52, and a FTIR optics/control modular assembly 54.

Figure 10:
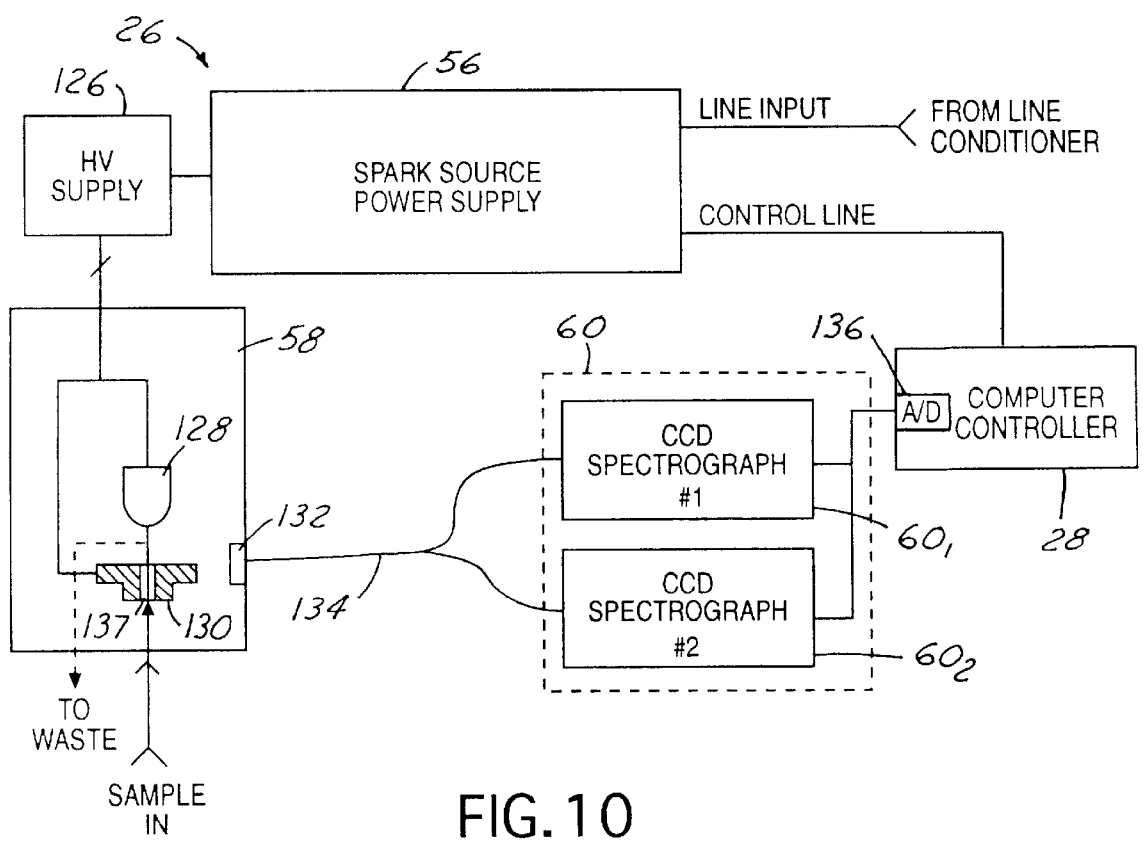
FIG. 10 is a diagrammatic and block diagram view showing, in greater detail, the optical emission spectrometer of FIG. 3.

In the illustrative embodiment, low resolution OES assembly 26 includes, from a packaging viewpoint, a spark source power supply 56, a spark stand enclosure 58, and a spectrometer portion 60 (diagrammatically illustrated in FIG. 10).

In a constructed embodiment, computer controller 28, is packaged to include a passive backplane incorporating a single board processor of the type equipped with all conventional forms of input/output (I/O) and device interfaces, such as for disk drives, graphics, and the like. Each of the measurement systems described herein communicate to computer controller 28 by way of a dedicated, custom interface board located on the passive backplane, or by way of a standard interface, such as an RS-232 serial port or a PC-104 interface. The computer controller 28 controls, and communicates with, the other subsystem and apparatus 10.

In the illustrative embodiment, apparatus 10 may include an in-line viscometer 30.

Figure 3:
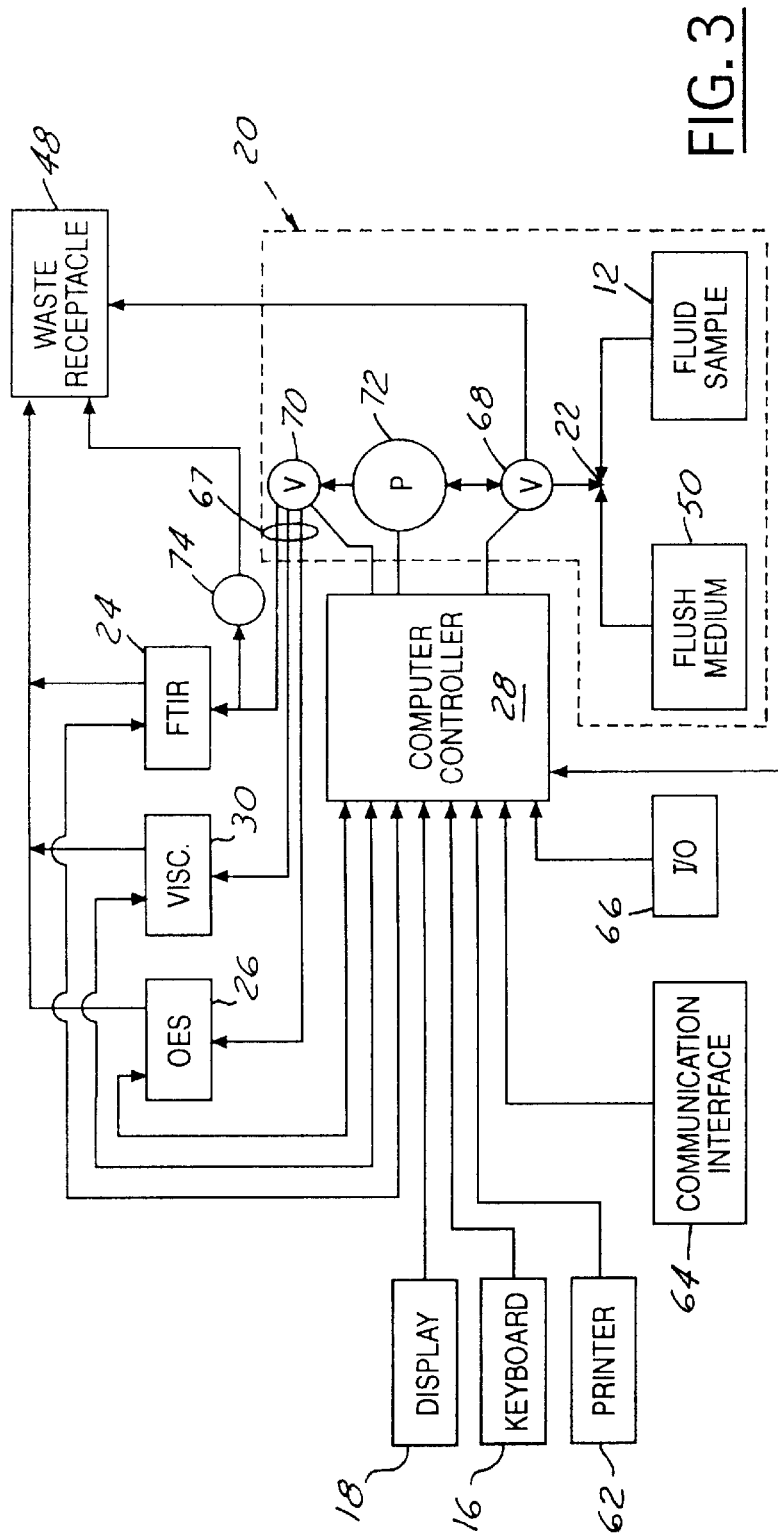
FIG. 3 is a simplified schematic and functional block diagram view of the apparatus of FIG. 1.

FIG. 3 shows a simplified functional block diagram of portions of apparatus 10. FIG. 3 further shows a printer 62, a communications interface 64, optionally, one or more other integrated analyzers 65 (shown in phantom line), and an I/O interface 66.

Keyboard 16 is connected to computer controller 28 and is provided generally to enable an operator to command predetermined functions, such as analyze, start, stop, and the like be performed. Keyboard 16 functions as a control panel for the apparatus 10.

Display 18 provides a visual user interface and is linked to the software component of the user interface executing on computer controller 28.

Transfer assembly 20 is configured to receive a fluid sample 12, and to selectively flow the fluid sample, under the control of computer controller 28, to an outlet 67 thereof. In a preferred embodiment, transfer assembly 20 includes a first multi-way valve, such as three-way valve 68, a second multi-way valve, such as 4-way valve 70, and a pump 72. Transfer assembly 20 avoids the need for use of a manifold. Use of multi-way valves reduces the space occupied by the transfer system, as well as the overall number of components needed for multi-directional fluid sample transfer and distribution. The pump 72, also under control of computer controller 28, is utilized for drawing in and distributing the fluid sample, air entrainment (for fluid sample removal) and for sample flushing by cleansing or flush medium 50. In particular, computer controller 28 controls both the speed and direction of pump 72. In a constructed embodiment, the speed and direction are user programmable. Transfer assembly 20, under the control of computer controller 28, is operative to perform following operations including but not limited to: fluid sample introduction, fluid sample direction to FTIR 24, OES 26, to waste receptacle 48, back-flushing (in the event of blockage), and cleansing. Apparatus 10 further includes a back pressure sensing/pressure relief valve 74 to protect the FTIR flow cell, thereby reducing the risk of cell fracture and/or leakage.

Infrared spectrometer, such as FTIR spectrometer system 24, is provided generally for optically testing the fluid sample 12 in generating a first data set in response thereto. FTIR spectrometer system 24 is connected to computer controller 28, and is controlled thereby. FTIR 24 further includes an inlet coupled to outlet 67 of the fluid transfer system. The FTIR spectrometer system 24 generally provides for measuring oil contaminants and wear products (physical parameters) in sample 12, such as oxidation, nitration, sulfation, fuel, water, glycol and soot. FTIR spectrometer system 24 may comprise conventional apparatus known in the art such as that provided by FTIR manufacturers such as Midac, Bomem, Designs & Prototypes, Analect, Nicolet, Mattson, Bruker, Perkin Elmer, and Bio-Rad. FTIR spectrometer system 24 produces an infrared spectrum of the sample 12 indicative of light absorption by sample 12 at different infrared frequencies, as generally known in the art. Empirical correlations translate intensity-versus-frequency (or wavelength) information to physical parameter values. Upon completion of an analysis, FTIR 24 provides computer controller 28 with the above-mentioned output data.

OES assembly 26 is coupled to outlet 67 to receive a portion of the fluid sample 12, and is configured to analyze the fluid sample and generate a second data set. The second data set preferably comprises an array of pixel values representative of spectral intensities in wavelength increments over a spectral range (i.e., is substantially continuously valued over at least a first predetermined wavelength range, or, for any particular spectrometer, overall of its range). OES assembly 26 generally tests for and measures wear metals, contaminant elements, and additive elements found in fluid sample 12. OES assembly 26 may comprise conventional and well-known apparatus commercially available in the art, such as available from CVI Laser and Control Development. In a constructed embodiment, OES 26 comprises a commercially available optical spectrometer, designated model SD2000, from Ocean Optics, Inc., 380 Main Street, Dunedin, Fla. 34698. OES assembly 26 is connected to and operates under the control of computer controller 28. The above-mentioned second data set is provided by OES 26 to computer controller 28 for subsequent analysis (e.g., determining "parts per million" of one or more constituent elements).

Computer controller 28 controls all functions of apparatus 10, providing hardware control, system diagnostics, user interface, database management, and data handling. Controller 28 in a preferred embodiment includes an open-architecture type system software, such as Windows 98 system software, commercially available from Microsoft, Redmond, Wash. As such, the environment is adapted for end-user customization for specific applications. The software which computer controller 28 executes is multi-layer in architecture, which is highly modular in design and highly customizable. "Methods" (i.e., organization or sequencing a functional operation) development has been reduced to a simple point-and-click function, and this includes sequencing of all functional operations such as valve switching, spark ignition, data acquisition (from any of the monitoring devices such as FTIR 24, and/or OES assembly 26), etc. Display and reporting functions are also easily customized to permit redesign of the user interface and the output of results. End-users may, in some embodiments, select the metals to be analyzed and the physical/chemical analyses to be included as output in the final report. For example, the end-user may select the foregoing from a list of available elements/tests.

In addition, computer controller 28 is programmed to provide a "Rules" editor for the expert system (to be described in further detail hereinafter) to enable straightforward updates thereto to satisfy the requirements and/or desires of specific markets and/or end-user applications.

Another added feature of the software involves automatic diagnostics that provide constant feedback to the operator in the form of status lights that indicate the condition and/or state of all functional components. A green status light indicates that a functional component is operating correctly. If the status changes, but the changing condition is not detrimental to the performance of apparatus 10, the specific status light turns the color yellow. In the event that a fault occurs, or a component fails to operate correctly, or if a disallowed operation is performed (such as the upper portion of housing 14 is raised by the operator while the power is on) the relevant status light(s) changes to the color red. A system diagnostics button shown on display 18 allows the operator to review the status of all components, and to receive information about any change in status, malfunction or failure. All main functional components provide some form of status information each time they are addressed and/or operated.

Viscometer 30 may be included to provide a direct measure of a viscosity value of fluid sample 12. Viscometer 30 is logically connected to and operates under the control of computer controller 28. Viscometer is physically coupled in-line to outlet 67 of the transfer assembly to receive a portion of fluid sample 12. Viscometer 30 is provided as an integrated unit with a viscometer sensor and a thermal control jacket for critical thermal control to a preset temperature. The viscometer measurement cavity is designed to provide efficient flush-out, ensuring sample turn-around within 1–3 minutes (for up to 90 weight oils). A single electronics interface board provides viscometer control, thermal control of the measurement head, signal handling and processing, and communications via a serial interface. For purposes of example only, an exemplary measuring range provided by viscometer 30 may be between about 5 to 100 centipoise (cP), at 100° centigrade.

Printer 62 may comprise conventional and well-known apparatus. Printer 62 is provided in connection with apparatus 10 for producing hard-copy output, such as producing an analysis reports for operators and/or end-user customers.

Communication interface 64 is provided for remote communications with apparatus 10. Communication interface 64 may comprise a conventional fax/modem for remote communications, or, in an alternate embodiment, comprise a conventional Ethernet interface. Apparatus 10 may be interrogated remotely for both operations and diagnostics, as well as for assessment of usage (e.g., for billing purposes).

In an embodiment using a standard fax/modem, communication between apparatus 10 (near end) and a far end device may be two-way. A first option involves apparatus 10 faxing analysis results, billing information or diagnostic data to a predetermined fax telephone number. This feature of the invention enables an end-user to transmit results directly to a client or a central office (for example), to send billing information to an assigned agent, or to send diagnostic data, in particular in the event of a component malfunction to a service bureau. A second option involves remote control wherein modem communication functionality provide remote access to control apparatus 10, acquire data, process results, as well as conduct system diagnostics.

In an embodiment incorporating an Ethernet network interface (or any other conventional network interface), the apparatus 10 forms a portion of a centralized or decentralized network. For example, an optional workstation (not shown) may be connected through network facilities to communications interface 64, and thence to the control system established by the software of apparatus 10. This network configuration offers several advantages, particularly to an end-user. The advantages of this configuration include: (1) allowing the end-user to pre-enter sample information remotely, via a standard computer; (2) enabling an end-user to customize apparatus 10, and to extend the reporting abilities thereof; (3) providing the ability to produce trend information, with statistical evaluation of the results; and, (4) providing an access to external networks (LANS, WANS, and remote networks).

Block 65, if included, may comprise alternate measuring devices or instruments (e.g., resistivity measuring device, densitometer, etc.).

I/O 66 may provide for the connection of, for example, a conventional external keyboard and mouse for the set up phase of apparatus 10, for carrying out service work, and/or for carrying out more extensive diagnostics. In addition, I/O 66 may provide an interface to a bar-code reader.

Figure 4:
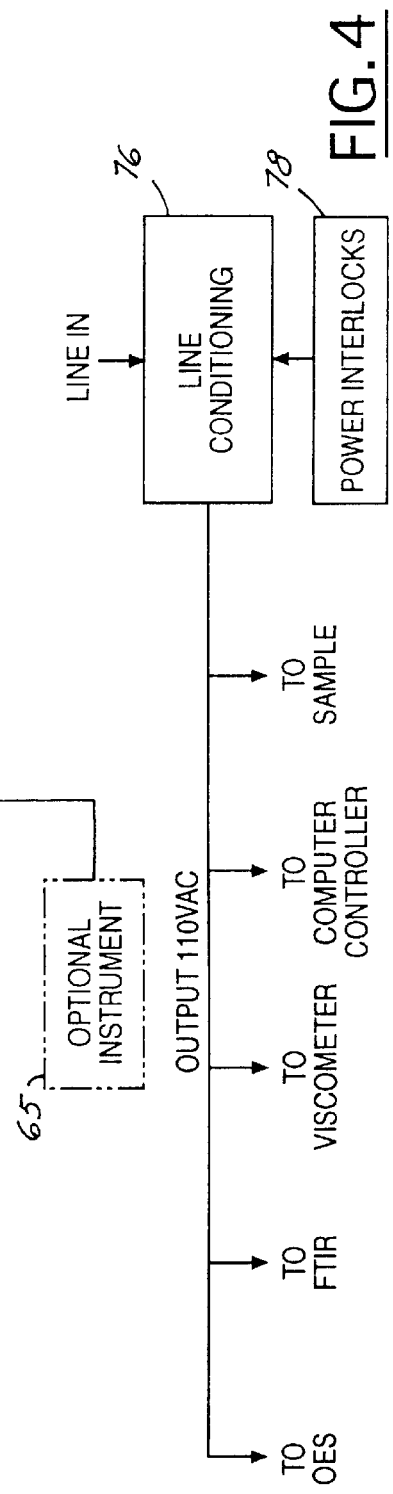
FIG. 4 is a simplified block diagram view of a power distribution schema used in the apparatus of FIG. 1.

FIG. 4 illustrates a power distribution system included in apparatus 10 which comprises a line conditioning device 76, and one or more power interlocks 78. Line conditioning device 76 protects apparatus 10 from voltage transients occurring on the input line. Certain covers, surfaces, and the like within housing 14 are protected by interlocks. The interlocks, when activated (e.g., by opening a cover), are operative to either defeat operation of the protected subsystem (e.g., prevent spark events from occurring in the spark stand) or remove power thereto. Each subsystem (as shown in FIG. 4) includes its own power supply, which uses the input line voltage. Accordingly, due to the power supply redundancy feature, failure of one power supply should not significantly effect operation of the other subsystem.

Figure 5:
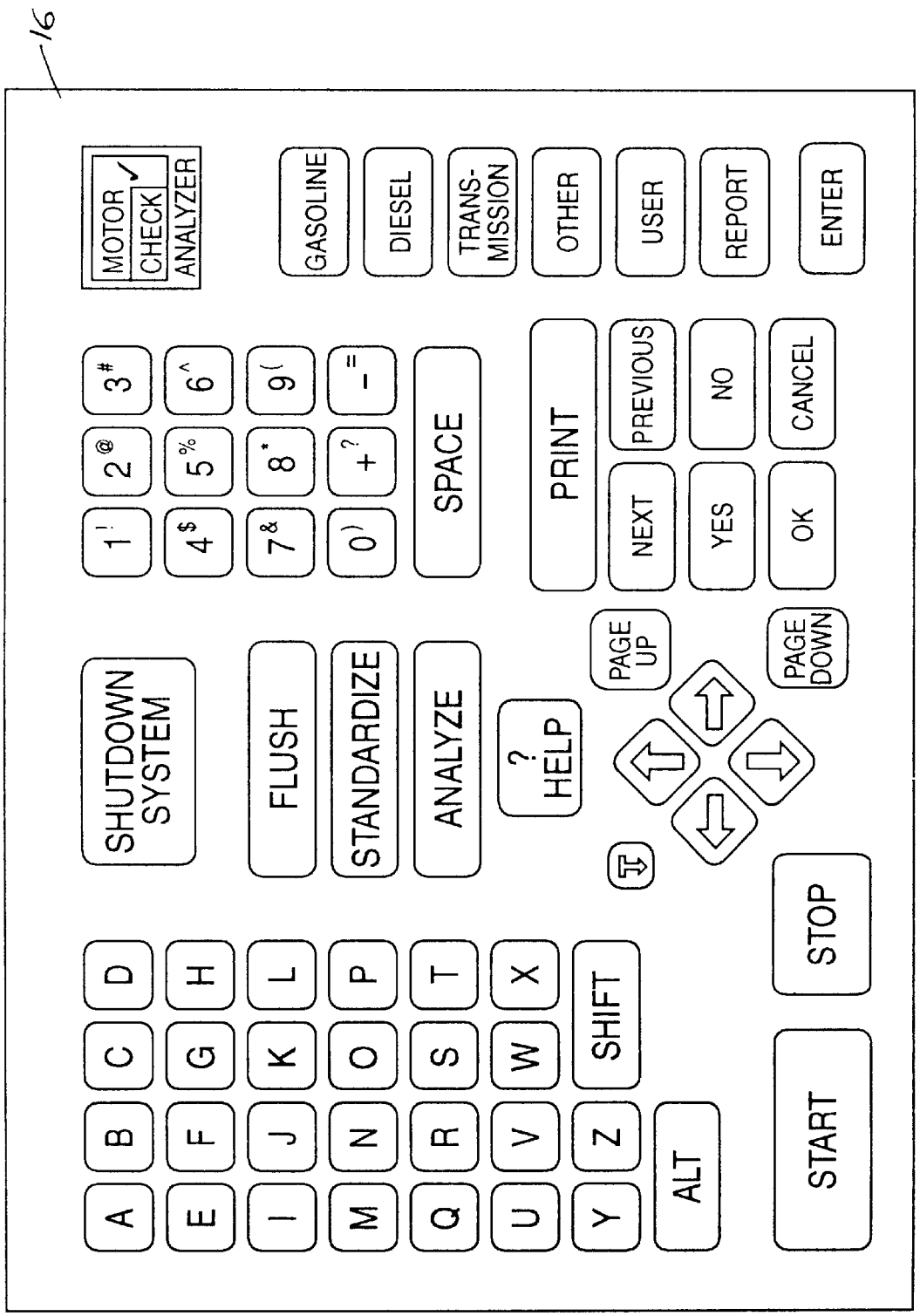
FIG. 5 is a simplified plan view showing, in greater detail, a keyboard portion of the apparatus of FIG. 1.

FIG. 5 shows keypad 16 in greater detail. As illustrated, keypad 16 provides all of the options and functions of a regular computer keyboard but, in addition, includes dedicated keys to initiate functions available on apparatus 10. Keypad 16 provides a more intuitive interface and minimizes keystrokes, thereby speeding up data entry. For example, as shown, there is a dedicated "GASOLINE" key for use in connection with gasoline engine vehicles.

In addition, certain ones of the keys are color coded wherein the color coding is linked to the color of the key representation on the system display 18. For example, the following keys are rendered in the color orange: "STOP", "PREVIOUS", "NO", and "CANCEL". The following keys are rendered in blue: "FLUSH", "STANDARDIZE", "ANALYZE", "HELP", "PRINT", "GASOLINE", "DIESEL", "TRANSMISSION", "OTHER", "USER", "REPORT", and the up, down, left, and right arrow keys. The "SHUTDOWN SYSTEM" key is rendered in the color red. The following keys are rendered in the color green: "START", "NEXT", "YES", "OKAY", and "ENTER". The remaining keys are rendered in one of two shades of grey. In a contemplated embodiment, keypad 16 may be implemented as a touch screen for preselected key functions.

Figure 6:
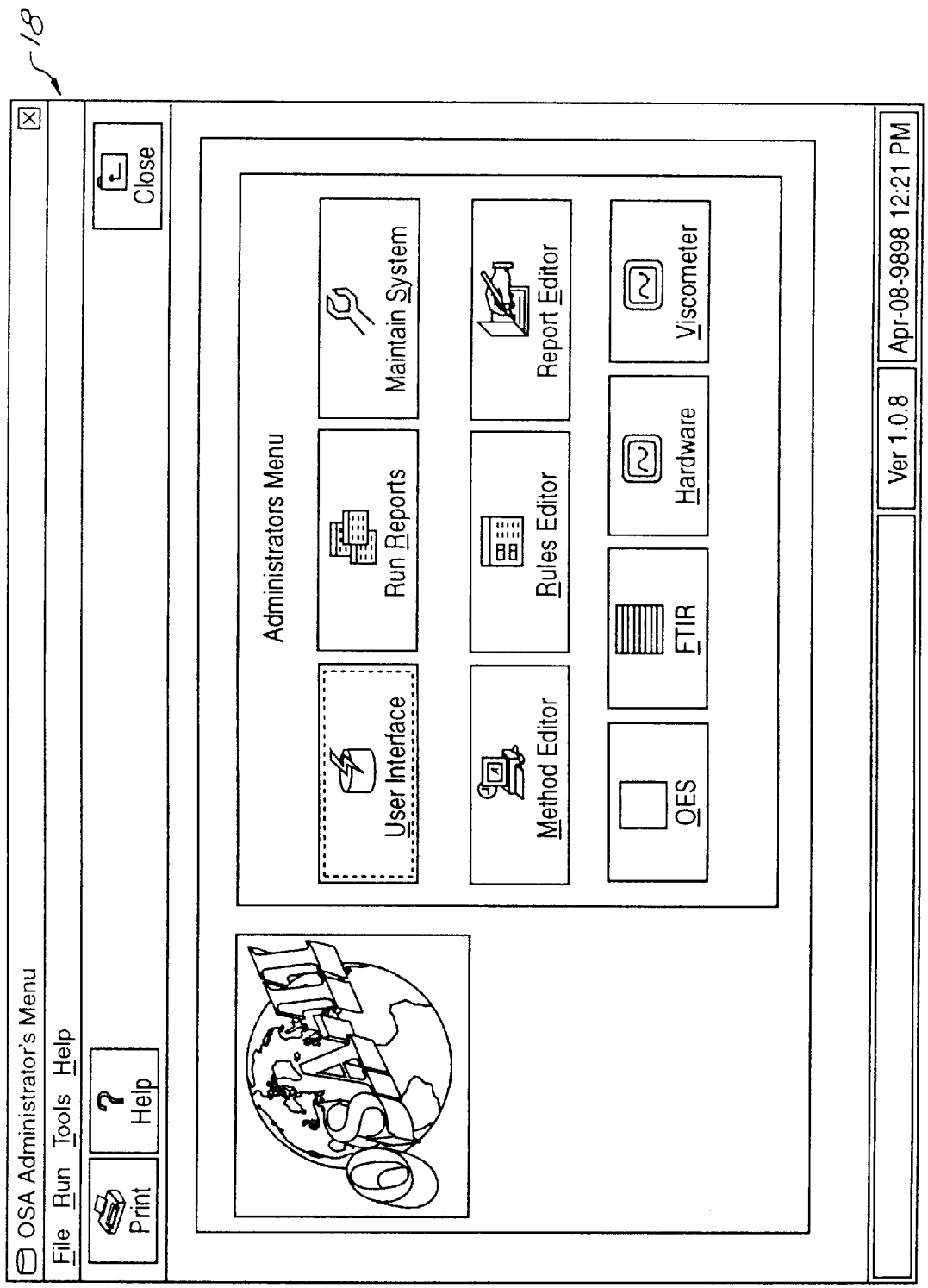
FIG. 6 is a simplified view illustrating, in greater detail, a screen display of the apparatus of FIG. 1.

FIG. 6 shows screen display 18 in greater detail. In a constructed embodiment, display 18 comprises a bright TFT (active matrix) style display.

Figure 7:
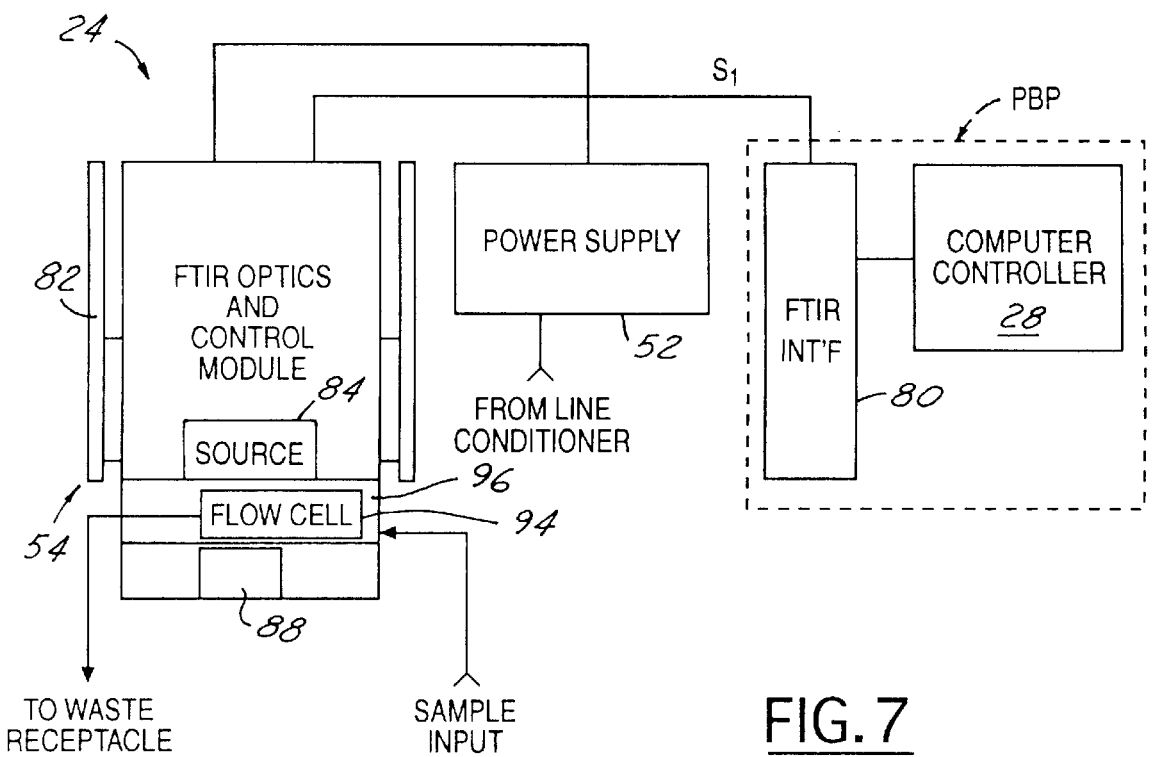
FIG. 7 is a simplified schematic and block diagram view showing, in greater detail, the FTIR assembly shown in block form in FIG. 3.

Referring now to FIG. 7, IR spectrometer assembly, such as FTIR spectrometer system 24, includes, in addition to FTIR power supply 52, and FTIR optics/control module assembly 54, an FTIR interface card 80 generating one or more control signals designated $S_1$, and a service slider arrangement 82.

Interface card 80, in a constructed embodiment, may be mechanically seated in the passive back plane referred to above, and as indicated in the dashed-line box in FIG. 7 designated "PBP". Service sliders 82 allow the assembly 54 to be moved for, among other things, service.

Optics and control module 54 includes an infrared (IR) light source, such as an IR source 84, which provides a modulated source of IR radiation, lens 86 (best shown in FIG. 9), a detector assembly 88 comprising a focusing mirror 90 and an IR detector 92 (best shown in FIG. 9), a flow cell assembly 94, and lateral translation means 96 for moving flow cell assembly 94 between first and second positions along a motion axis designated "M".

Figure 9:
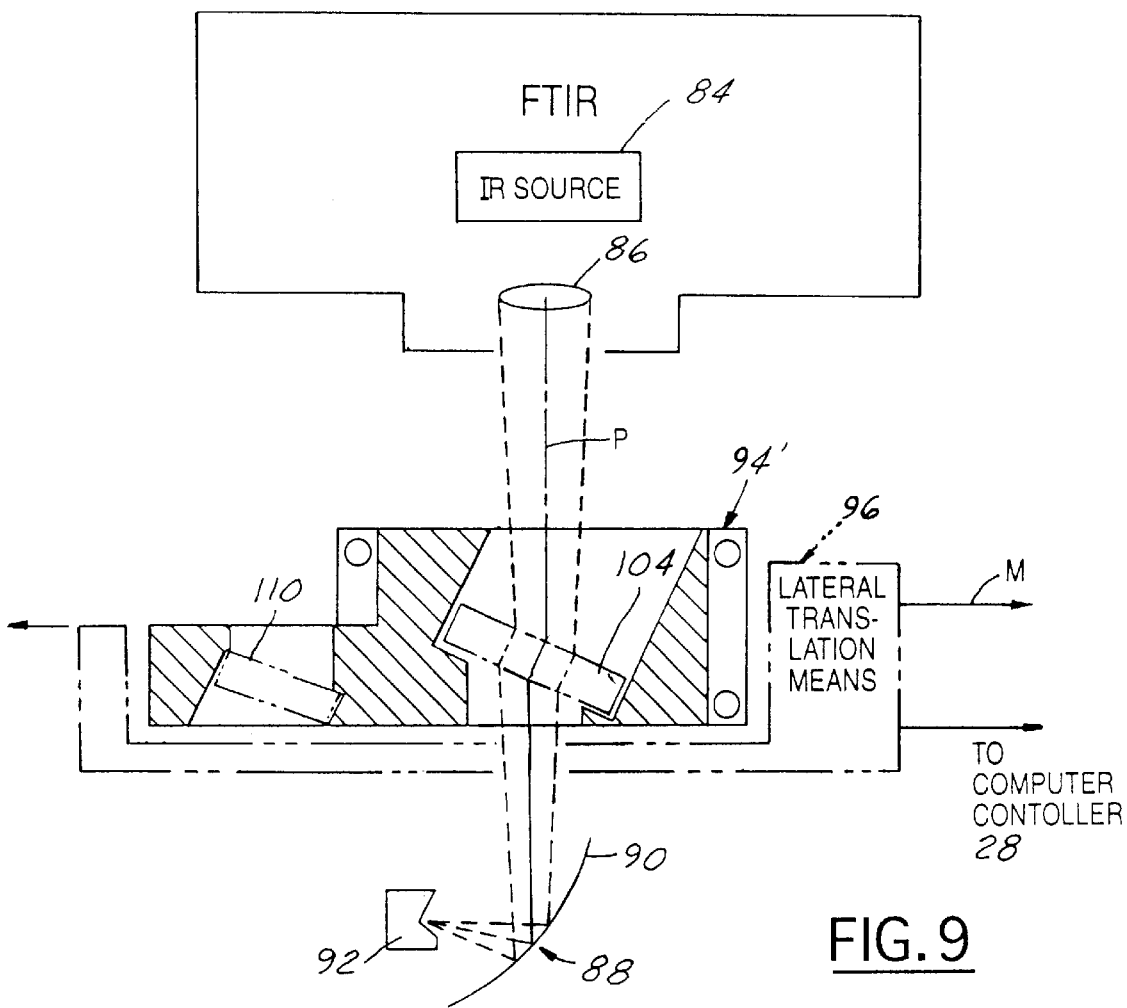
FIG. 9 is a block diagram view of the FTIR assembly shown in FIG. 7.

As best shown in FIG. 9, IR source 84 is configured, by way of lens 86, to generate an infrared (IR) radiation beam focused along a principal axis to converge. The envelope of the IR radiation beam is identified by the dashed line in FIG. 9, while the principal axis is designated as "P". The detector assembly 88 is spaced apart from the IR source 84. In a preferred embodiment, lens 86 comprises zinc selenide material, includes a Broad Band anti-reflection (BBAR) coating, and has a relatively small focal length lens. The use of zinc selenide material for lens 86 (as well as for the flow cell optical components) improves resistance to attack from atmospheric moisture, thereby enabling apparatus 10 to be used in relatively humid environments. Significantly, the use of a short focal length lens minimizes the free air space between the main interferometer housing (i.e., the IR source housing), the flow cell assembly 94 and detector assembly 88, which, in a constructed embodiment, typically extends no more than about 1" (2.5 centimeters). This short free air space in turn reduces spectral interferences from water vapor. In addition, an important distance for reducing space is the distance from the IR source lens 86 to the detector assembly 88, and may be about 3.5" in a constructed embodiment.

Focusing mirror 90 may comprise conventional well-known apparatus commercially available in the art.

Detector 92 may comprise conventional detector apparatus known in the art, and may comprise a TGS detector 92. In a constructed embodiment, TGS detector 92 comprises a 1.3 millimeter target size detector element for improved sensitivity (signal-to-noise).

Flow cell assembly 94 is translatable along motion axis "M", which extends transversely of principal axis "P", by way of lateral translation means 96.

Lateral translation means 96 may comprise conventional and well-known structure available in the art, and is connected to and under control of computer controller 28. Lateral translation means 96 is provided for automated collection of instrument background data, which may be a unique, potentially time-variant characteristic of FTIR system 24. That is, flow cell assembly may periodically be moved to a first position wherein the compensator window is intermediate, and preferably aligned to, the IR source and the detector, and wherein reference measurements may be taken.

In accordance with another aspect of the present invention, an inventive flow cell assembly 94 is provided which reduces or minimizes the undesired effects of "fringing" (to be described hereinafter). As background, typically, infrared transmission or flow cells are placed in a zone where the IR radiation is collimated. Light emerging from the interferometer of a Fourier Transform Infrared spectrometer may already be parallel and used for illuminating the optical cell containing the sample for study. The lens can then focus the light from the absorption region and refocus it onto a detector. The detector may include additional optics, but this added structure only enhances the ability of the system to image the infrared absorption zone of the cell on to the detector.

The problem of fringing may be encountered when well-polished plane, parallel surfaces are at normal incidence to the IR beam. Conventional flow cells have a sandwich-like structure: a pair of IR transmissive plates between which is disposed a spacer which is usually the volume occupied by the sample. Light is reflected at every transition. If the distance, as measured in optical terms (i.e., including the effects of the index of refraction of the absorption medium) is about equal to an integral number of half-wavelengths of the incident light, a situation known as "standing waves" will occur. Standing waves lead to a characteristic sinusoidal "fringe pattern" which is imposed on to the actual signal being measured. The process of multiple reflections at the corresponding multiple optical interfaces will be reinforced at the resonance wavelengths (or the corresponding frequencies) determined by the spacing. For a distance of D cm spacing, with an index of refraction of the sample of n, the period in wavenumber units is: $1/(2 \, Dn) \, cm^{-1}$. Thus, for a 0.1 mm cell (i.e., spacer thickness), the period is $50/n$ $cm^{-1}$. For indices of refraction ranging from 1 to 2, the fringe spacing is between about 25 to 50 $cm^{-1}$. This fluctuating signal may be comparable to the width of desired spectral features. The fringing interference is therefore an undesirable artifact.

In accordance with the invention, a tilt angle is built into the flow cell assembly 94 so that incident light beams are reflected in a direction out of the optical path.

Figure 8A:
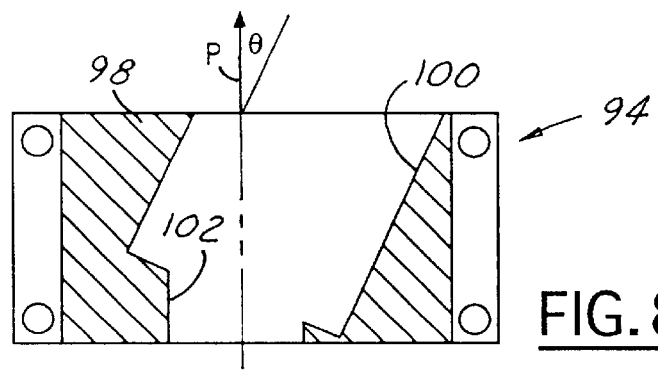
FIG. 8A is a simplified cross-sectional view of a first embodiment of the flow cell assembly shown in block form in FIG. 7.

FIG. 8A shows a first flow cell assembly embodiment showing the built-in tilt angle. Flow cell assembly 94 includes a base 98, for example made from aluminum, a first bore 100, and a second bore 102. Optical plates forming the sample cell are sized to be accommodated in first bore 100 (similar to that shown in FIG. 8B for flow cell 94' to be described hereinafter). The tilt angle (described below) causes reflections of the incident IR radiation to be directed out of the optical path.

Figure 8B:
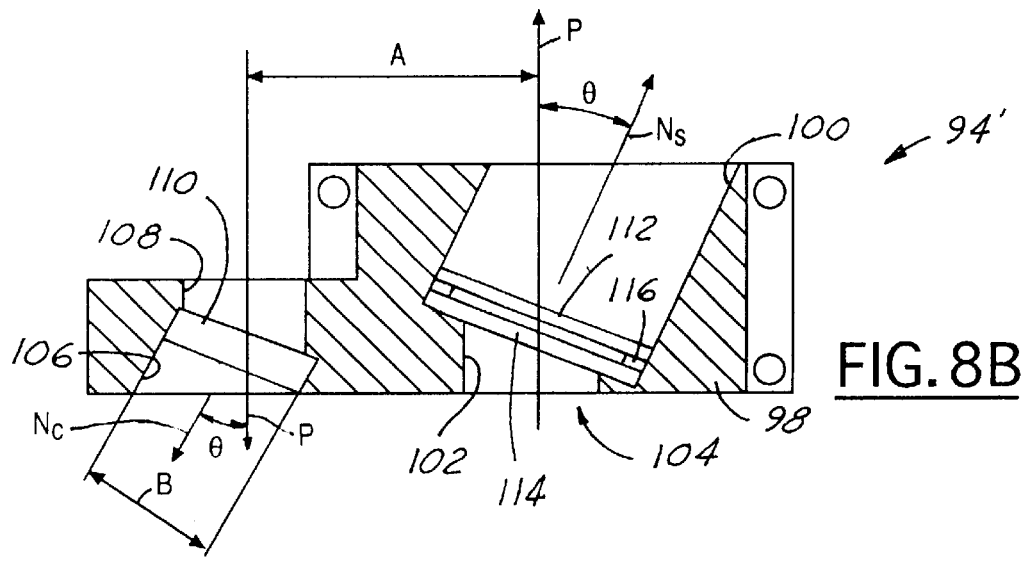
FIG. 8B is a simplified, cross-sectional view of a preferred embodiment of the flow cell assembly shown in block form in FIG. 7.

FIG. 8B, however, shows a preferred flow cell assembly embodiment 94' having a built-in compensator window. Flow cell assembly 94', in addition to base 98, first bore 100, second bore 102, includes a sample cell 104, a third bore 106, a fourth bore 108, and a compensator window or plate 110. Sample cell 104 includes a first optical plate 112, a second optical plate 114, and a spacer 116.

Plates 110, 112, and 114, preferably comprise zinc selenide (ZnSe) material, but may alternatively be formed using any other relatively high index of refraction materials, such as Ge, Si, AMTIR, CdTe, and the like. Spacer 116 is, in a preferred embodiment, approximately 0.1 mm thick. Each one of sample cell 104 and compensator window 110 have associated therewith a respective normal axis, designated $N_s$ and $N_c$, respectively. IR radiation typically propagates along a principal axis designated P in FIG. 8B. In accordance with the invention, sample cell 104 and compensator cell 110 are each tilted a tilt angle θ, which may be between about 15 degrees and 50 degrees, preferably between 20 degrees and 40 degrees, more preferably between about 20 degrees and 25 degrees, and most preferably about 20 degrees in a constructed embodiment. Selecting the tilt angle to reduce undesirably fringing artifacts depends on a variety of factors including, but not limited to, the optical materials used (e.g., for the optical elements), whether the optical element is coated, and the spectral features of interest. Preferably, the effective thickness of compensator window 110 is substantially the same as the effective thickness of sample cell 104 as well as the respective indices of refraction (relative to the filled sample cell).

Figure 8C:
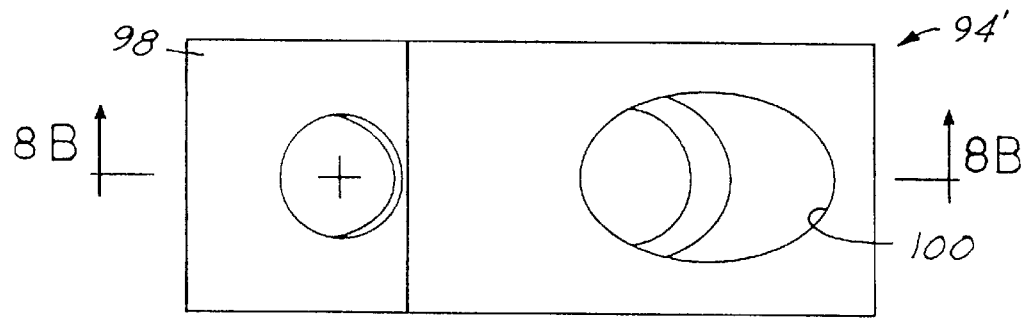
FIG. 8C is a simplified, top view, relative to the orientation illustrated in FIG. 8B, of the preferred flow cell embodiment.

FIG. 8C shows a view of flow cell assembly 94' as viewed from the top relative to the orientation depicted in FIG. 8B.

Figure 8D:
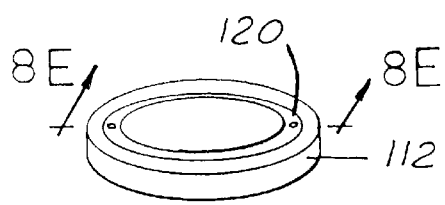
FIG. 8D is a simplified perspective view of an optical plate of a sample cell portion of the flow cell assembly shown in FIG. 8B.

FIG. 8D shows a perspective view of first plate 112. First plate 112 includes a pair of bores 118 extending through the thickness thereof (which in a constructed embodiment is approximately 2 mm thick, 32 mm (approximately 1.25") in diameter), and a circumferential groove 120. Compensator window 110, in the described embodiment, comprises zinc selenide material, is approximately 25 mm in diameter, and approximately 4 mm thick.

Figure 8E:
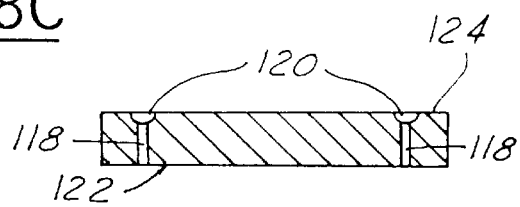
FIG. 8E is a simplified, cross-sectional view of the optical plate FIG. 8D, taken substantially along lines 8E—8E.

FIG. 8E is a cross sectional view taken substantially along lines designated 8E—8E illustrated in FIG. 8D. Plate 112 includes a first surface 122, and a second surface 124. Given the orientation shown in FIG. 8B, second surface 124 faces second plate 114, while first surface 122 defines the first surface upon which IR radiation impinges from IR source 84. Fluid sample 12 may be introduced through a small tube disposed or in communication with one of bores 118 to thereby fill the void between plates 112, 114 established by spacer 116, and thence flow out of the other one of bores 118 into an outlet tube coupled to waste receptacle 48. Groove 120 provides a path for particles larger than the spacer thickness (e.g., as constructed, 0.1 mm) to flow from input to output without blocking the flow of the fluid sample.

Lateral translation means 96, as shown in FIG. 9, is coupled to and is controlled by controller 28 to move flow cell assembly 94' between a first position wherein compensator window 110 is optically intermediate IR source/lens 84/86 and detector assembly 88, and a second position (as shown in FIG. 9) wherein sample cell 104 is optically intermediate IR source 84/lens 86, and detector assembly 88. The first position is used by apparatus 10 when a background or reference reading is desired. Regular collection of the background insures optimum photometric performance and increased baseline stability of the system.

It should be understood that the described FTIR system is atypical inasmuch as it uses a convergent IR radiation beam, and not a collimated or parallel propagating type beam. It should further be understood that use of such a convergent radiation beam directly leads to an advantage of a more compact system, as described above. However, due to the convergent nature of the IR beam, along with the tilting of sample cell 104, and the further relatively high index of refraction of sample cell 104, an actual displacement (as well as defocusing) of the image through the sample cell occurs (this is an exaggerated shift to the left in FIG. 9). It should be understood that the detector 92 is selected, and is located spatially, optimally, for the arrangement as illustrated in FIG. 9 (i.e., sample cell in place—the second position). A background or reference reading taken through air, or even through an untilted cell would allow the beam to pass through without changing direction. Without such a change in direction (i.e., spatial translation, ultimately), the IR radiation beam, when taking the background reading, would miss, or perhaps only imperfectly impinge on detector 92 (as positioned for readings through the sample cell).

Therefore, in accordance with yet another aspect of the present invention, the compensator window 110 is made of the same material, having approximately the same thickness and index of refraction, and further, is disposed at approximately the same tilt angle, as the sample cell 104. Producing substantially identical conditions for beam refraction in the compensator window as for the sample cell means: that the focused images of both the sample beam and the reference (background) beam will coincide in space at the selected detector location. Without this aspect of the invention, a larger detector would have to be used to effectively capture both beams (an alternate embodiment required a 2 mm target area instead of a 1.3 mm target area detector for the embodiment using flow cell assembly 94'). Such an enlarged detector has shown a reduced sensitivity (signal-to-noise) by up to a factor of 2. In sum, by matching the overall properties of thickness and index of refraction for both the sample cell, and the compensator window, the detector 92 can remain fixed in space as lateral translation means 96 moves the flow cell assembly between the first and second positions.

Of course, alternate configurations are possible for compensator window 110, in terms of the composition of materials used, thicknesses, index of refraction, etc. that are within the reach of one of ordinary skill in the art, and are included within the spirit and scope of the present invention.

FIG. 10 shows, in greater detail, OES assembly 26. In addition to spark source power supply 56, enclosure 58, and spectrometer assembly 60, OES assembly 26 further includes a high voltage supply 126, an upper electrode 128, a lower electrode 130, a collimator 132, a bifurcated fiber optic cable 134, and wherein spectrometer assembly 60 includes a first spectrometer $60_1$, and a second spectrometer $60_2$. Assembly 26 also includes an analog-to-digital conversion and interface card 136, which may be mechanically disposed in the passive back plane and intelligently linked with the software of apparatus 10 by way of appropriate software drivers.

Spark source power supply 56 and HV supply 126 may comprise conventional apparatus. Applicants commercially obtained the same from Arun Technology Ltd., Unit 16, Southwater Industrial Estate, Station Road, Douthwater, West Sussex, England, under part number: ATL410911. Electrodes 128 and 130 are preferably made primarily of silver material. However, other materials may be used, such as, for example, tungsten.

FIG. 10 further shows transfer assembly 20, which causes fluid sample 12 to flow through a through-bore 137 portion of lower electrode 130, and thence to waste receptacle 48. Computer controller 28 controls application of high voltage across electrodes 128/130 to thereby generate a spark. The frequency of sparking is programmable and may be varied by the operator by appropriate selection of a spark frequency parameter value. Spark frequencies may include 120, 150, 200, 250, 300, 350, 400, and 450 Hz.

FIG. 10 further shows collimator 132, which may comprise conventional apparatus, such as is available from General Fiber Optics, a subsidiary of Sigma-Netics, of One Washington Avenue, Fairfield, N.J. 07006. The bifurcated cable 134 and collimator 132 are, in a constructed embodiment, provided together as a unit. Together, they function to acquire light emitted in the region of electrodes 128/130, and carry that light to both spectrometer $60_1$, and spectrometer $60_2$.

First spectrometer $60_1$ is configured to receive the light or radiation generated by electrodes 128/130 and generate a first spectral pattern in response thereto. Second spectrometer $60_2$ is configured to receive substantially the same light or radiation as the first spectrometer and generate a second spectral pattern. In a preferred embodiment, the second spectral pattern is different from the first spectral pattern in both spectral range covered as well as resolution.

Spectrometers $60_1$ and $60_2$ may comprise conventional and known, commercially available optical emission spectrometers. In a constructed embodiment, the spectrometers $60_1$ and $60_2$ are a model SD 2000 commercially available from Ocean Optics, Inc., Dunedin, Fla., USA. In a preferred embodiment, spectrometer $60_1$ is configured with a resolution of approximately 0.3 nm across a spectral range from about 200 nm to about 340 nm. This constitutes primarily the UV range. Spectrometer $60_2$ has a resolution of approximately 1.0 nm and is configured to produce a spectral pattern over a spectral range nominally between about 180 nm to 880 nm (constitutes UV-visible range). In the constructed embodiment, each spectrum is imaged using a 2048 pixel charge couple device (CCD) array spectrograph. Of course, functionally equivalent sensing devices may be substituted and remain within the spirit and scope of the invention.

A/D converter 136 may comprise conventional and known apparatus. A/D converter 136 is provided for receiving a substantially analog signal corresponding to the charge accumulated on the pixels of the CCD sensor during an exposure time, and converting each into a respective digital word. For example, each digital word may be a twelve-bit digital word. Software drivers are available, for example from Ocean Optics for their products, that enable one of ordinary skill in the art to use the spectrometer output from higher level software programs. In one embodiment, the output of first and second spectrometer $60_1$ and $60_2$ each comprise a text file. The text file may include two columns. The first column may include an increasing series of wavelength values corresponding to the 2048 pixels in the CCD. The second column may include a series a values representing an intensity or magnitude at the corresponding wavelength. The software drivers orchestrate the coordination of the sampling of the analog signal presented to A/D 136 from spectrometers $60_1$ and $60_2$. In the constructed embodiment, the spectrometers arrive from the manufacturer pre-calibrated. That is, each spectrometer $60_1$ has associated therewith a predetermined calibration equation (e.g., in quadratic form) that provides the wavelength value of column 1 as a function of pixel number. This is why the wavelength value of column 1 corresponds to the pixel numbers (i.e., via the calibration equation).

Typical spectrometers used as atomic emission spectrometers generally feature larger, higher resolution instruments, such as those having a resolution of 0.05 nm or better ("high resolution"). The spectrometers employed in apparatus 10 are considered "low resolution" spectrometers, in view of the foregoing stated resolutions.

First spectrometer $60_1$ is used for most of the wear metals and dirt and contaminate elements (i.e., for detection, and for concentration determination). Second spectrometer $60_2$ is used, in a constructed embodiment, for two basic purposes. The first purpose involves determining elements in the visible spectrum, notably sodium and potassium, which do not require higher resolutions for adequate detection and may not be covered in the wavelength range of first spectrometer $60_1$. Second, for the determination of wear metals at high concentrations. In the later case, the second spectrometer $60_2$ enables apparatus 10 to provide an extended dynamic range, thereby detecting both high and low concentrations of wear metals and contaminate elements, essentially simultaneously, without the need to reset the spectrometer gain, thereby eliminating the need for effectively redundant measurements.

It should be understood that the resolution of both spectrometers $60_1$ and $60_2$ are much lower than conventionally considered sufficient for determination of elemental emission lines. However, the use of full spectral presentation (i.e., substantially continuously valued over a wavelength range, as opposed to using higher resolution instruments with single photo multiplier tubes coupled with a large monochromator that detect particular emission lines) enables apparatus 10 to implement numerical data processing techniques, such as peak area integration, curve resolution and curve fitting, and full or partial spectral fitting, and regression analysis. The latter feature corresponds to either classical least squares fitting methods, or multivariate statistical methods, such as PCA (principal components analysis), PCR (principal components regression), PLS (partial least square), LWR (locally weighted regression) methods, or neural networks. The methods noted, as well as other approaches to univariate or multivariate analysis, applied as described below on the acquired sample spectral data, enable the analysis of analyte components (i.e., fluid sample constituents) that would otherwise remain unresolved.

In operation, fluid sample 12 is excited by the spark. When the electrons of the atoms of the constituent materials (as well as the fluid sample) contained therein, are driven to higher energy states by the electrical discharge, they are in an unstable state. When the electrons eventually relax to a ground state, photons are emitted. The energy—or wavelength—of these photons is indicative of the particular atom responsible for the emission. Thus, the detection of light at that wavelength is an indication of the presence of that particular atom in the sample. Moreover, the more light emitted under conditions of constant electrical excitation, the more of these particular atoms are present in the sample. The relationship between concentration and intensity is substantially linear (monotonically increasing) over a very wide dynamic range; provided, however, that the excitation strength is relatively constant. This is difficult to achieve using spark as the excitation source.

Thus, in accordance with yet another aspect of the present invention, methods and apparatus are provided to condition raw spectral data to produce stable, informationally significant sample spectral data.

Raw spectral data from the spectrometers generally takes the form of an array of pixel values representative of wavelengths and associated spectral intensities over a predetermined spectral range. As noted above, each ordered pixel number may have a wavelength associated therewith based on a preexisting calibration equation. Variability in both the wavelength (i.e., wavelength shift) and intensity present challenges overcome by this aspect of the present invention.

Wavelength shift may occur due to (i) the inability to make spectrometers that are physically identical; and (ii) external conditions such as temperature, humidity, atmospheric pressure, vibration, and electrical pick-up (which may result in wavelength calibration changing as a function of time). Variation in the intensity of certain emission lines over multiple sample spectra (even for the same sample—same concentration level—taken closely in time) may occur in the OES portion of apparatus 10, primarily due to the use of spark or arc emission technology, in which a constant strength of excitation is difficult to achieve.

It thus bears emphasizing that disturbances that allow a drift in the sample spectral data in the wavelength axis render subsequent mathematical analysis more complicated or impossible. This is because particular spectral emission lines (or spectral features) of interest may be confused or mistaken for other irrelevant features. Moreover, spectral emission lines which overlap (due to the "low resolution" of the spectrometers used) are much more difficult to decompose in the presence of drifting spectral emission lines. Therefore, for the raw sample spectral data to be compatible with both (i) the data taken on other apparatuses 10, and (ii) the data taken on the particular apparatus 10 as a function of time, the relationship between pixel number and wavelength (i.e., "wavelength calibration") must remain substantially constant (i.e., no appreciable pixel to wavelength shift).

In accordance with the invention, the OES portion of apparatus 10 uses radiation from spark emission to produce a spectral pattern having spectral features, such as emission lines, to quantify constituents in a fluid sample. The emitted radiation, in addition to relating to atoms of the fluid sample constituents (e.g., wear metals, additives, and the like), define spectra including a plurality of spectral features such as emission lines, indicative, at least in part, of (i) the composition of the electrodes, which in the preferred embodiment comprise silver material, and (ii) hydrocarbons in the lubricant itself. Of course, to the extent that electrodes 128/130 are comprised primarily of an alternate material, such as tungsten, the background spectrum would be different, and include a plurality of spectral features indicative of tungsten. An additional plurality of spectral features would be present for an alternate electrode material and/or combination/alloys thereof.

The plurality of spectral features, such as emission lines, for silver have a pre-existing, predetermined known wavelength values. These known spectral features, due to the composition of the electrodes themselves, may be considered absolute wavelength standards for the operation of apparatus 10. The acquired sample spectrum of a fluid sample generated by the spectrometer of apparatus 10 may be regularized (with respect to wavelength drift) by reference to one or more of these spectral features drawn from the background.

X-Axis (Wavelength) Correction

X-axis correction is achieved generally by first establishing a mapping between wavelength and pixel position using spectra exhibiting known absolute wavelengths. This allows spectral determinations to be conducted in wavelength space as opposed to pixel space. In wavelength space, the positions of multitudes of emission lines of different elements are well known, whereas, the ability to locate needed spectral information is much more difficult when the x-axis is labeled only by pixel number.

To effect this mapping, one can exploit the existence of the "background" emission lines always present in spark emission spectra generated on the emission spectrometer on apparatus 10. This is completed by respectively correlating respective a pixel position of a set of background emission lines in a spectrum and known wavelengths using regression techniques. This mapping establishes a standard wavelength for each pixel. For example, if one had 2048 pixel values, a set of 2048 wavelengths would be generated and the wavelength position of the set of background emission lines are known with respect to this standard set of wavelengths.

In a constructed embodiment, wavelength drift, if any, is corrected by performing the following steps, designated by reference numerals 145–148 in FIG. 18. In addition, the examples to follow are generally with reference to spectrometer $60_1$, (0.3 nm resolution). It should be understood, however, that the same principles apply to spectral processing with respect to spectrometer $60_2$ as well (e.g., 1.0 nm resolution).

The first step, step 145, involves defining a background spectrum having a plurality of spectral features (e.g., emission lines) indicative at least in part of the composition of the electrodes. The term "background spectrum" is defined in the foregoing paragraphs. This step may be performed by the substep of taking an inventory of the multitude of spectral features that make up the background spectrum for a particular configuration (e.g., silver electrodes). Some of these spectral features may be better than others for X-axis correction so a selection step may be performed (see below). This defining step is generally performed before the apparatus 10 is deployed to analyze samples.

The second step, step 146, involves selecting at least one, and preferably a plurality of, background spectral features (e.g., multiple emission lines) from the plurality of spectral features that make up the background spectrum (e.g., in the illustrated embodiment, the spectrum indicative of the silver composition of spark electrodes 128/130). Each one of the selected emission lines has a known wavelength. In a constructed embodiment, the selected emission lines comprise the 224.64 nm, 241.32 nm, 243.78 nm, 247.86 nm and 335.98 nm emission lines. Of course, in any particular embodiment, other emission lines and/or spectral features of the background spectrum may be used. This step is generally performed before an apparatus 10 is deployed for sample analysis. It is preferable to use a set of lines which span the entire spectral range.

The third step, step 147, involves, after acquiring a sample spectrum, determining respective wavelength values for the set of background emission lines. The raw spectral data of the fluid sample, may comprise an n-row (where n=number of pixels, e.g., 2048), two-column array of data. Each row contains a wavelength value and a corresponding intensity value. For spectrometer $60_1$, the wavelength values may span approximately 200–340 nm, while for spectrometer $60_2$, the wavelength values may span approximately 180–880 nm. As described hereinbefore, the wavelength values in the array may be derived from using a pixel number in connection with a calibration equation that is "built-in" to the spectrometer (or associated therewith ahead of time through software).

Depending on wavelength accuracy needed, wavelength determination may be determined in a number of ways. In one embodiment, the standard wavelength point corresponding to the maximum of the emission line may be used. That is, identifying an emission line may involve locating a "peak" or "maximum" intensity within a relatively small wavelength range. This may be done using any known mathematical analysis. In a constructed embodiment, for example, apparatus 10, through programmed software, examines a predetermined number of intensity values for a local maximum in a range where the sought-after background emission line is likely to be found. Once the local "peak" is identified, the corresponding wavelength value, as indicated in that row of the data array, defines the actual location (wavelength) of the sought-after emission line. The foregoing wavelength value determination procedure provides x-axis calibration accuracy to within about 1 pixel, since the procedure simply identifies the row (i.e., pixel) having the "peak" intensity within a range. For higher accuracy, algorithms can be used to better determine the wavelength value corresponding to the emission line (peak) maximum. This can be done using known mathematical analysis for peak fitting. For example, the peak line profile may be "fit" to a well defined functional form, such as a Gaussian lineshape, or a more empirical version of peak fitting (such as described above) or such as that of LaGrange interpolation or a cubic spline might be employed. For example, since there are 2048 pixels (i.e., data points) spread out over about 140 nm of spectral range in the illustrated embodiment of spectrometer $60_1$, a nominal pixel spacing is about 0.07 nm/pixel. Moreover, since the resolution of spectrometer $60_1$, is about 0.3 nm, the raw spectral data includes, theoretically, a little over 4 data points (pixels) per resolution. Since an emission line will be represented as being no thinner than about 0.3 nm, there will be at least 4 data points thereover. Moreover, in practice, a particular emission line may span as many as 6–10 data points (pixels). These data points can be "fit", for example, using a cubic spline or any other known fitting technique. The result of the "fit" is an equation that can be used to determine the actual wavelength value of the "peak", "mean" or other identification criteria of the sought-after emission line in the sample spectrum. This approach provides the capability to determine wavelength values "in-between" rows (i.e., pixels) of the data array, and thus provides an accuracy of greater than 1 pixel. This step is performed for each spectral feature (e.g., silver emission line) selected as an internal absolute standard for apparatus 10.

The fourth step, step 148, involves, generally, translating the sample spectrum with respect to wavelength based on a correction to the internal, absolute wavelength standard. The translating step may include four (4) basic substeps: determining offsets for each emission line, determining a total wavelength offset for the sample spectrum, converting from wavelength space to pixel space (i.e., generating a pixel shift number), and shifting the intensity values in the acquired sample spectrum.

The first substep involves determining a wavelength offset for each background spectral feature (e.g., emission line), each taken between (i) the expected wavelength value of a background emission line (based on known absolute standards), and (ii) the actual, measured wavelength value (i.e., actual location) of the background emission line as indicated in the sample spectrum. In the foregoing example, if the location of the "224.64 nm" silver emission line, as indicated by the sample data is 225.64 nm, then there is a 1 nm shift to the right. In a constructed embodiment, determining offsets is done for each emission line being used as an absolute wavelength standard.

The second substep involves determining a composite wavelength offset for the acquired sample spectrum. This is completed by using wavelength offsets for all the emission lines used as absolute wavelength standards. In a constructed embodiment, a simple arithmetic average of the individual wavelength offsets is employed to determine the composite wavelength. For example, to determine an average wavelength offset, each offset (in wavelength terms, e.g., 1 nm) is assigned an orientation (e.g. to the right (+) or left (−)). Then, an arithmetic average is taken.

The third substep involves converting the average offset calculated above in wavelength space to pixel space. To convert the average wavelength offset to a pixel shift, the arithmetic average is converted to pixels using the nominal pixel spacing of 2048 pixels/(340−200)nm=14.6 pixels/nm (assuming spectrometer $60_1$). For example, an average wavelength offset of +2 nm converts to about 29 pixels. This value is a pixel shift number, and the orientation is to the right.

The fourth substep, which actually achieves the x-axis correction, involves shifting each intensity value in the column of intensity values in the data array (i.e., sample spectrum) by the calculated pixel shift number, either up or down. The wavelength correction process may be accomplished immediately after the sample data acquisition of the fluid sample without further data acquisition, inasmuch as the background spectral features (e.g., the silver emission lines that act as wavelength standards) are acquired simultaneously with the sample data. Moreover, in this case, the background emission lines are "naturally" occurring as a result of the experimental configuration (i.e., due, in part, to the material or composition of the electrodes) and therefore no external standard needs to be added.

In an alternate x-axis correction embodiment, accuracy greater than 1 pixel may be obtained. First, the manufacturer's calibration of spectrometers $60_1$, and $60_2$ may be replaced by running various constituents, preferably the wear metals of interest, through apparatus 10. These constituents will exhibit emission lines having known wavelength values, as published in the known literature. The resulting spectral data obtained thereby may be analyzed and a relationship between wavelength and pixel number may be obtained. For example, for a third-order fit:

$$\lambda = \alpha P + \beta P^2 + \gamma P^3 + \Delta$$

Once this process has been performed, spectral features (which include emission lines) may be selected from the background spectrum for use as wavelength standards during sample acquisition and analysis. For example, where silver is used for the electrodes 128/130, emission lines capable of being resolved by spectrometers $60_1$, and $60_2$ may be used (as in the constructed embodiment). However, the alternative embodiment is not as limited, and may include any spectral feature (e.g., several emission lines, indicative of the electrode material, that are too close together to be uniquely resolved so they therefore appear as a "bump"—this "bump" may be selected as a spectral feature). This spectral feature may not have a predetermined, known absolute wavelength associated therewith available in the literature. However, an absolute wavelength value can nonetheless be assigned to the spectral feature, so that it can be used just like an emission line as follows. The background spectral feature has a number of data points (pixel no.: intensity) associated therewith. These data points may be analyzed to find a "peak", "mean", or other meaningful representation of the spectral feature. For example, the "peak" may be expressed as pixel number (e.g., both integral and fractional parts thereof). The pixel number of the "peak" may then be substituted into the above equation to yield a wavelength value ("secondary wavelength standard"). This standard may then be carried forward for use during acquisition and analysis of a sample.

Next, analysis of the fluid sample results in raw spectral data being provided to apparatus 10 (e.g., in the form of wavelength value: intensity value for the 2048 pixels). The plurality of "spectral features" are then identified in the sample spectrum, and, using the same "peak" detection algorithm, a corresponding plurality of spectral feature locations are generated (e.g., pixel number xxx.xx as the location of the spectral feature as indicated by the array of values). Since the "absolute wavelength" of these selected spectral features has not changed (i.e., they are absolute), a new calibration equation may be derived by any known fitting procedure. That is, apparatus 10 now has available a plurality of ordered pairs of data in form of ($APL_1$: $\lambda_1$; $APL_2$:$\lambda_2$, ..., $APL_n$:$\lambda_n$), where $APL_i$ is the actual pixel location of spectral feature i from the sample spectrum array, and, $\lambda_i$ is the absolute wavelength associated with spectral feature i. Thus, an equation providing $\lambda$ as a function of P (pixel number) may be produced ("new calibration equation").

Next, using the new calibration equation, the array of raw spectral data, which is in the form of wavelength (old calibration):intensity, may be translated or mapped with respect to wavelength to an x-axis corrected array. This translation is done by applying the new equation to each data point in the raw data spectrum. That is, the intensity for each point will remain the same, but the wavelength value will be recomputed by substituting pixel numbers into the new equation to obtain new wavelength values. For example, for pixel number=1, evaluate the new equation for the first data point and associate the new wavelength value with $I_1$ (intensity for data point number 1). Next, substituting pixel number=2 and associating the resulting wavelength value with I2, and so on.

At this point, apparatus 10 has available to its software a spectrum of the fluid sample, corrected with respect to wavelength to compensate, for example, for drift. However, the spacing between points may not be uniform, since the new calibration equation will in many instances be non-linear.

Therefore, a further step may be performed so that all the data points (e.g., 2048 points expressed in wavelength value: intensity form) are evenly spaced as a function of wavelength. For example, the spacing may be selected to uniformly cover the spectral range. Thus, for spectrometer $60_1$, with a spectral range of 140 nm (340–200 nm) and 2048 pixels, the spacing should be about 0.07 nm. Thus, after standardizing, which may be accomplished by conventional interpolation techniques, the data points will be uniformly spaced (e.g., 200.00 nm: $I_1$; 200.07 nm: $I_2$; 200.14 nm: $I_3$, etc.). Standardizing (i.e., imposing the x-axis corrected sample spectral data on a uniformly spaced grid) simplifies later arithmetic operations, to be described in detail hereinafter. This set of standardized wavelengths can then be considered the standard set of wavelengths for all spectrometers.

Y-Axis (Intensity) Normalization

With respect to intensity variation, it bears repeating that establishing a uniform excitation strength spark emission is a circumstance difficult to achieve in practice. This variation introduces challenges solved by the present invention, inasmuch as the linear relationship between emission line intensity and constituent concentration (i.e., "concentration" is the parameter that the expert system needs as an input) is dependent on a constant strength of excitation.

Figure 11:
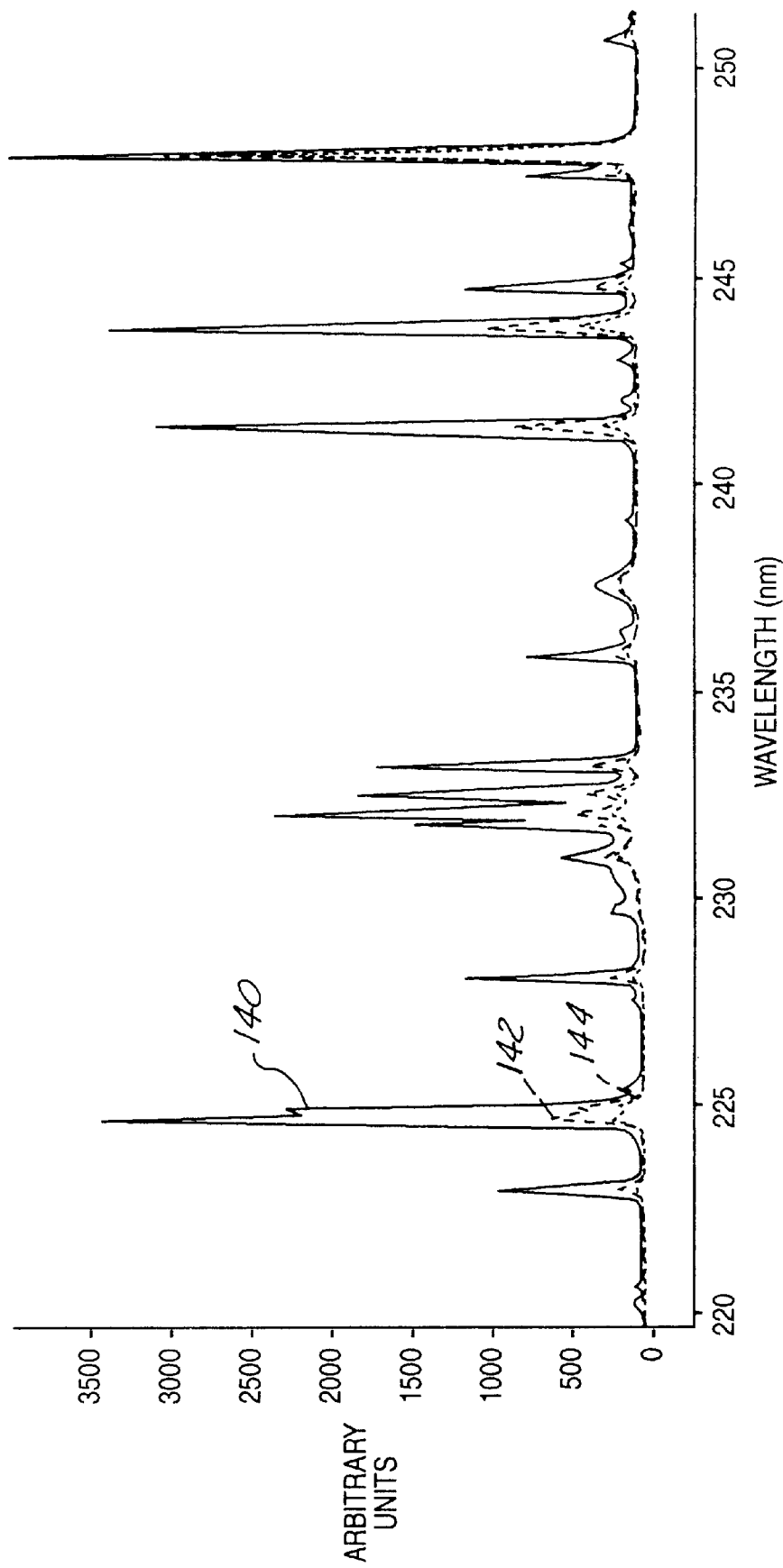
FIG. 11 is a wavelength-versus-intensity spectral pattern illustrating intensity variation for the OES.

By way of example, FIG. 11 shows three background reference spectra 140, 142 and 144 taken from three different samples of clean, base oils (i.e., simple mineral oils without additives). Based on FIG. 11, one might reasonably believe that the entire electrode emission strength varies by a factor of 5 or more.

Figure 12:
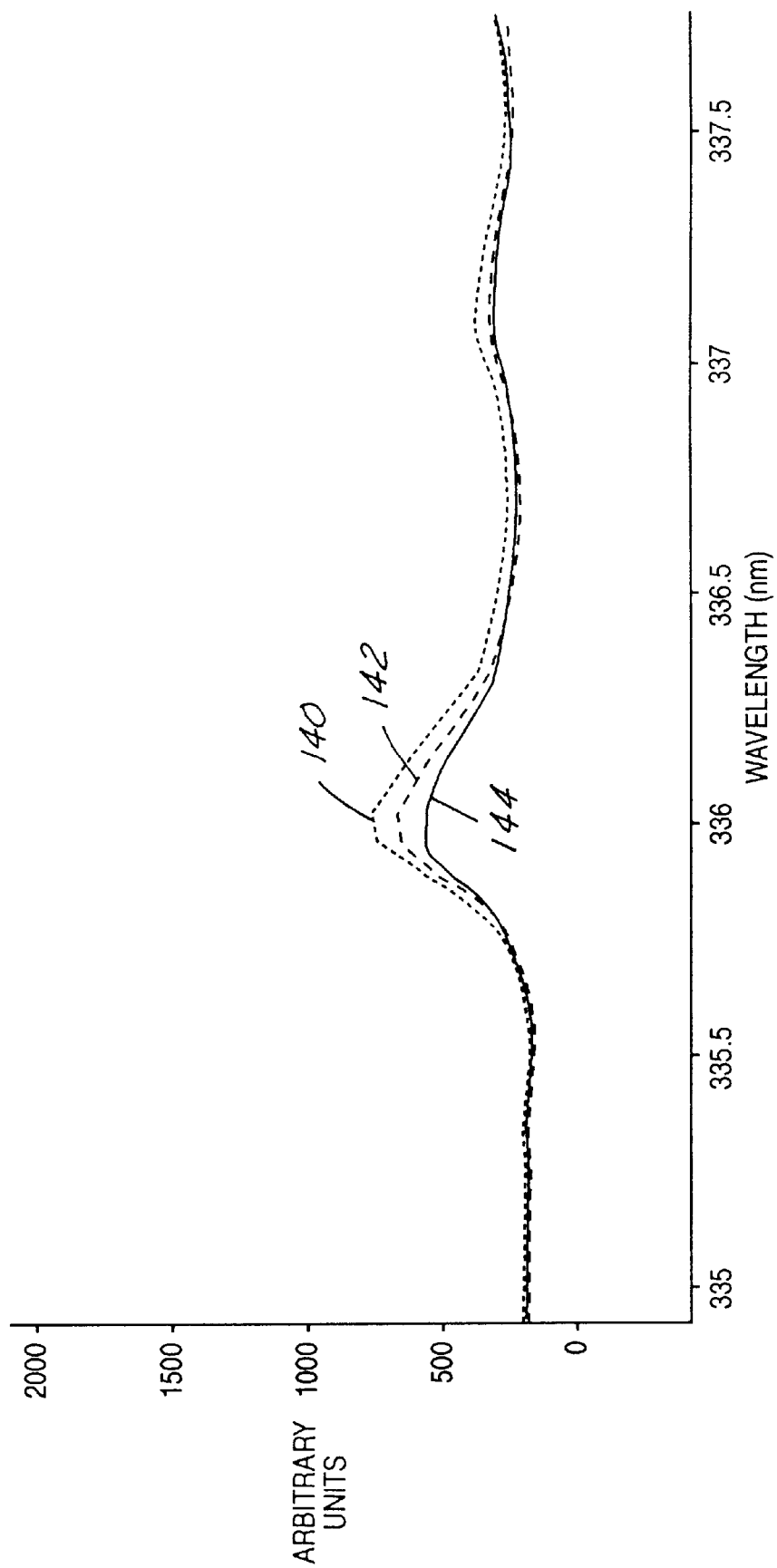
FIG. 12 is the spectral pattern of FIG. 11 at the red end about an emission line suitable for intensity normalization.

While FIG. 11 illustrates the three reference spectra at the blue end of the spectrum (220–250 nm), FIG. 12 shows the same three sample spectra 140, 142 and 144 with emphasis on the red end (335–338 nm wavelength range). Note that the variation in intensity is relatively reduced.

In accordance with still yet another aspect of the present invention, the variation in the emission strengths or intensities of constituents (or analytes) to be measured, which is caused by variability of the spark (i.e., electrical discharge), may be reduced by using the intensity of a background spectral feature, such as an emission line (i.e., one associated or indicative at least in part with the material of the electrodes) for normalization. In a constructed embodiment, the intensity of the 336 nm silver "emission line" is used as a normalizing quantity. The emission line "intensity" comprises, in the constructed embodiment, the area under the curve for the 336 silver emission line (as shown in FIG. 12) in the acquired sample spectrum.

Not all emission lines associated with the composition of the electrodes are desirable or useful in reducing intensity variation. However, in accordance with the present invention, a method is provided for normalizing an intensity of a constituent emission line of a measured element from the acquired sample spectrum of a fluid sample generated by a spectrometer having a pair of electrodes. FIG. 19 shows a flowchart diagram of the method in steps 149–151. The method includes two basic steps. The first step, step 149, involves selecting at least one spectral feature, such as an emission line, from a background spectrum having a plurality of spectral features (e.g., emission lines) indicative at least in part of the composition of the electrodes and/or base oil or similar solvent carrier wherein the selected spectral feature (e.g., emission line) has an intensity variation characteristic. The second step includes normalizing the intensity of a constituent emission line of a measured element with respect to sample spectrum with respect to the "intensity" of the selected spectral feature (e.g., emission line). This second step involves a measuring step, as shown in step 150, and a transforming step, as shown in step 151. In step 150 (FIG. 19), an intensity of the background spectral feature (e.g., emission line) is measured. In step 151, the sample spectrum is transformed with respect to intensity in accordance with the measured intensity of the selected background spectral feature.

It bears repeating that the intensity of some, but not all, background spectral features (such as emission lines) of a background spectrum correlate to the emission line intensity of constituents in a fluid sample to be measured and can be used for normalization. Normalization by, for example, ratioing the emission line intensity of an element to that of a background line results in (i) a reduced variability and hence an improved elemental concentration determination and (ii) a measurement that can be determined adequately in a shorter period of time (i.e., less signal averaging necessary).

Accordingly, in yet another aspect of the present invention, a method for selecting the background spectral feature (such as an emission line) having a desirable intensity variation reduction characteristic is provided. This method may be performed prior to the run time analysis of a fluid sample, so that all the run-time software has to do is to look up the established background spectral feature (e.g., emission line). The approach is to evaluate several candidate background spectral features (e.g., emission lines) for their respective capabilities to reduce variation of the intensity of a constituent of interest.

The first step involves identifying an emission line associated with at least one constituent in a fluid sample. For example, the selected emission line may be the 324 nm emission line associated with copper, a measured wear metal.

The second step involves selecting a first set of spectral features (e.g., emission lines) from the plurality of spectral features (e.g., emission lines) associated with the background spectrum. The first set includes the likely candidates of background spectral features that might be used as a normalizing standard. The first set may include simply just one emission line.

The third step involves obtaining a predetermined number of spectra of the fluid sample, preferably a single fluid sample. The fluid sample preferably contains the above-mentioned constituent (e.g., copper) of a known concentration. The predetermined number of spectra should preferably be statistically significant, and may be at least 20 spectra, preferably at least 30 spectra, most preferably at least 50 spectra. However, using a higher number of spectra will generate results that are more statistically significant.

The fourth step involves determining a first intensity variation of the emission line associated with only the constituent (i.e., the 324 nm copper emission line) over the predetermined number of spectra. For example, over a predetermined number of spectra for a fluid sample, which contained a constant concentration of the constituent copper, the observed intensity variation, where the electrodes were controlled to a spark rate of 120 discharges of per second, was approximately twenty percent (20%) (notwithstanding a constant concentration of copper, and further, replicate measurements done closely in time).

The fifth step involves assessing how effective each candidate is at reducing variation. This step involves determining, for each spectral feature (e.g., emission line) in the first set, a respective second intensity variation over the same set of replicate spectra. In a preferred embodiment, this step comprises two substeps: (i) for each of the predetermined number of spectrum mentioned above, dividing the "intensity" of the emission line of the constituent by the intensity of the respective background spectral feature (e.g., emission line) in the first set to thereby produce a predetermined number of ratio values; and (ii) calculating a second intensity variation using the predetermined number of ratio values.

For example, for each of the predetermined number of spectra, the "intensity" of the copper emission line is divided by the "intensity" of the background emission lines in the first set (e.g., the 336 nm silver emission line as well as any other candidates in the first set) to develop a series of ratio values. The variation of this series is then determined and associated with the respective background spectral feature (e.g., 336 silver emission line). For example, when the intensity of the 324 nm copper emission line is divided by the intensity of, for example, the 336 nm silver emission line, the resulting variation, over the predetermined number of sample spectra, was, in one configuration, approximately eight (8%) percent.

The sixth step involves selecting emission lines from the first set that have a second intensity variation that is less than the first intensity variation to thereby form a second set of emission lines for possible use for normalization. For example, since the variation in intensity of the normalized 324 nm copper emission line using the 336 nm silver emission line (8%), is less than the variation in the intensity of the 324 nm copper emission line without any normalization (e.g., as noted above, approximately 20%), the 336 nm silver emission line represents a satisfactory standard to use in reducing intensity variation of spark emission spectra. The 336 silver line thereby goes into the second set of emission lines.

The seventh and final step for selecting a background spectral feature (e.g., emission line) suitable for intensity normalization involves selecting one of the spectral features from the second set based on predetermined criteria. One criteria comprises the degree to which variation is reduced.

EXAMPLE

Determining Concentration of a Wear Metal

Figures 13A, 13B:
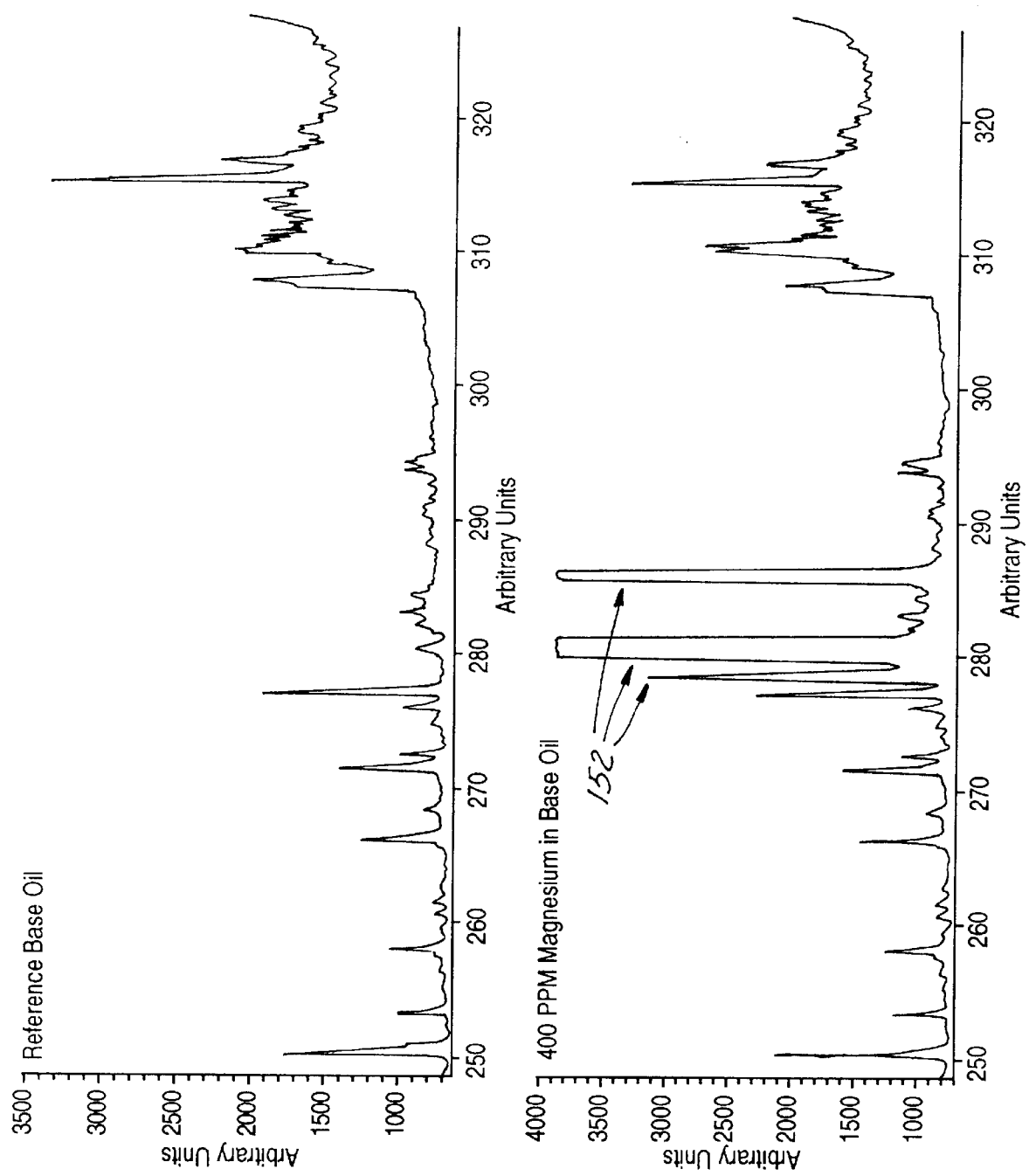
FIGS. 13A–13B illustrate a typical wavelength-versus-intensity spectral pattern for the OES for a reference base oil without and with an additive.
Figure 14:
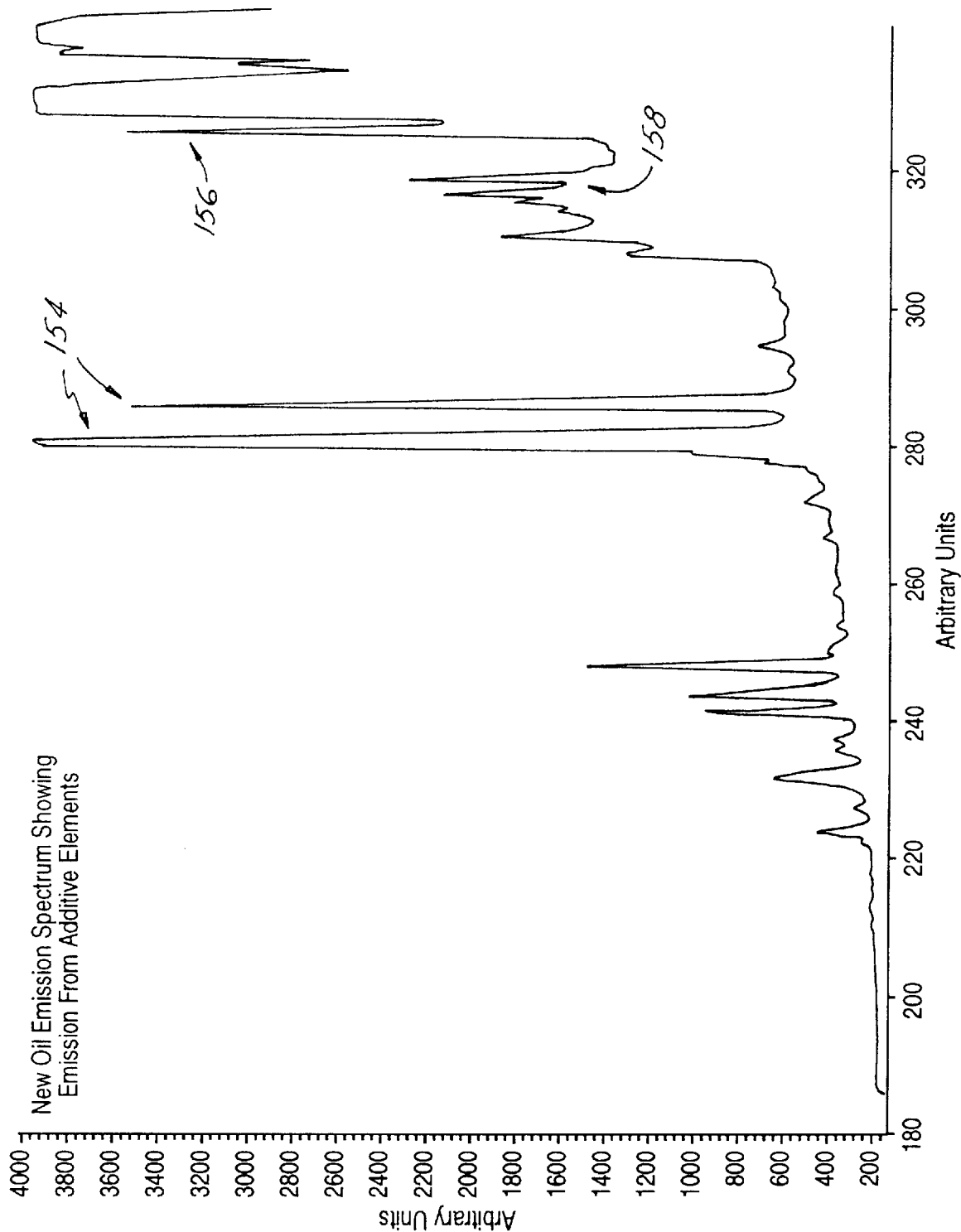
FIG. 14 illustrates a reference oil with multiple additives.
Figure 15A:
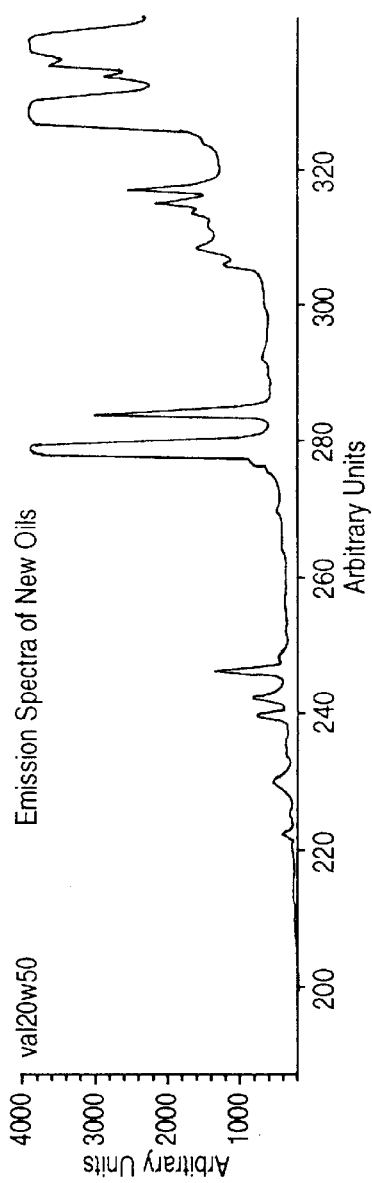
FIGS. 15A–15C illustrate emission spectra for various new oils.
Figure 15B:
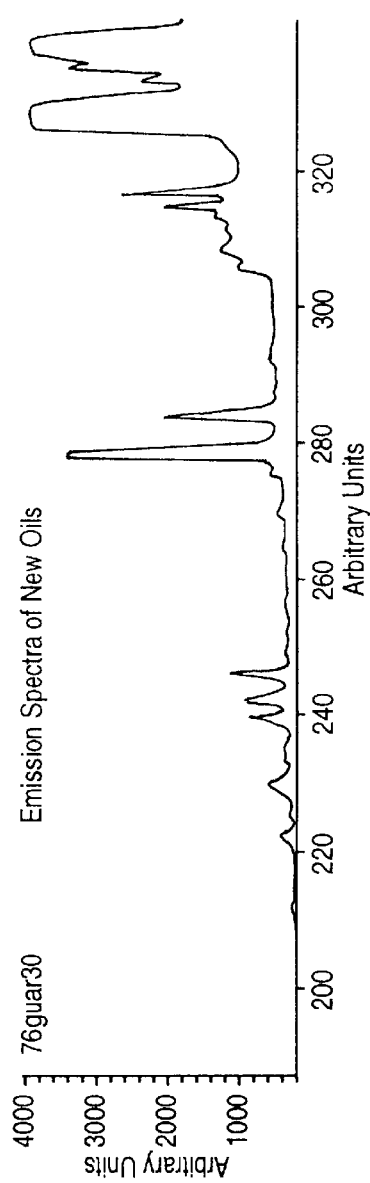
Figure 15C:
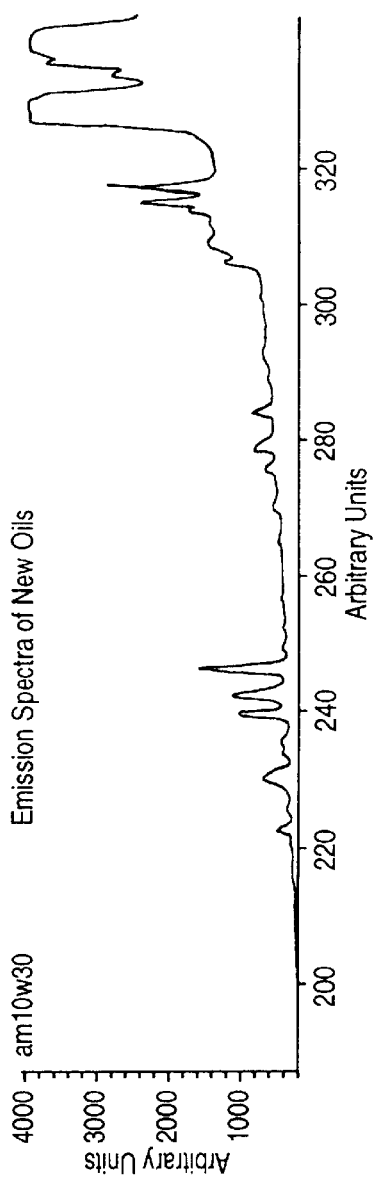

This example pertains to the determination of the concentration of copper in a used engine oil sample. The first or preliminary step may involve identifying a background spectrum having a plurality of spectral features indicative at least in part of a composition of the electrodes. For example, FIG. 13A shows the spectrum of a reference base oil or mineral oil. Most of the emissions are a property of the electrodes. FIG. 13B shows the effect of additives which are often present in new oils. Emission lines 152, for example, correspond to the additive magnesium. Emission lines 152 may also be useful as emission lines having a known, absolute wavelength for purposes of correcting for wavelength drift as described above under the heading "X-AXIS CORRECTION". FIG. 14 illustrates a further example of a new oil having magnesium additive emission lines 154, copper additive emission lines 156, and calcium additive emission lines 158. FIGS. 15A–15C show further exemplar spectra of three different "new" oils. The foregoing spectra, as well as spectra from other new oils can be stored in the memory of apparatus 10 for subsequent use. This step does not need to be performed during run time, and preferably is done in advance thereof. In one embodiment, the background spectra are standardized (i.e., uniform wavelength spacing).

Next, an intensity calibration curve is built. This curve will be used for correlating intensity to a concentration. This may be done empirically. For example, a known concentration of a constituent is introduced into apparatus 10 and analyzed. Next, a selected reference spectrum (e.g., FIGS. 13, 14 and 15) is subtracted from the raw spectral data resulting from the analysis. This spectral substraction is explained in detail below. Next, the resulting "peak" intensity of a spectral feature (such as an emission line associated with the constituent for which the curve is being built) is then correlated to the known concentration. In a constructed, preferred embodiment, the area under the curve representing the emission line peak is measured and is associated with the corresponding known concentration. This is done for all the constituents to be analyzed by apparatus 10. This step is preferably done ahead of the time when a sample is analyzed. The plurality of intensity calibration curves may be stored in non-volatile memory, such as on magnetic media for subsequent use.

Next, a spectral feature of the background spectrum is selected for use as a normalizing ratio. This may be done as set forth above under "Y-AXIS Correction". In a preferred embodiment, the area under the curve of the 336nm silver emission line is used, based on its ability to reduce intensity variation.

Next, the fluid sample under test is introduced into apparatus 10 and analyzed thereby, including analysis by OES assembly 26. The resulting raw spectral data is then corrected for x-axis drift, if any, as described above, and is illustrated in steps 145–148 of FIG. 18.

The next steps involve determining a characteristic emission line associated with the selected constituent element of interest in the example, namely copper. In this example, the characteristic emission line may be the 324 nm emission line. What emission line to choose may depend on what lines are strongly indicative of copper, whether there exists or expected to exist interfering elements (i.e., elements that have emission lines that are located close or nearby to the selected constituent emission line) in the sample under test. The spectral feature selected to represent the targeted constituent may correspond to the spectral feature used to generate the above-mentioned intensity calibration curves.

Next, a spectral subtraction step is performed which involves subtracting a reference spectrum (i.e., of the type illustrated in FIGS. 13A–13B, FIG. 14 and FIG. 15A–15C) from the sample spectrum. This spectral subtraction step minimizes and/or eliminates undesirable and/or unrequited background emission lines, and so long as there is spectral registry (accomplished by X-axis correction), a simple subtraction may be done to perform this step. Since the stored reference spectra are unscaled, an adjustment to the intensity of the reference spectrum to be subtracted must be made. This adjustment may be made by locating a spectral space where there are no significant spectral features, such as, for example, around 300 nanometers. Then, adjusting the amplitude of the reference spectrum until the subtraction in the located spectral space nulls (i.e., produces a true zero difference). In practice, a series of scaled reference spectra (e.g., 1.1*reference, 1.0*reference, 0.9*reference, 0.8*reference, etc.) are each subtracted and the resulting region is analyzed. The best (i.e., lowest average amplitude—noise) is used.

In addition, regarding spectral registry, it should be understood that the subtraction process can be performed, numerically, in a variety of ways. For example, in a constructed embodiment, both the reference spectra and the sample spectrum comprise 2048 data points. The subtraction may thus be performed on a point-per-point basis (i.e., point 1 (sample)—point 1 (reference)). The sample spectrum may have different wavelength values, on a per point basis, than the reference spectra. However, the wavelength divergence may not be substantial enough to cause serious difficulties in locating spectral features. In an alternate embodiment, however, both the reference spectra and the sample spectrum are standardized prior to subtraction (i.e., each have the same starting wavelength value, and each have the same, uniform, wavelength value spacing between data pairs).

The next step involves measuring the area under the silver 336 nm spectral feature.

The next step involves measuring the area under the 324 nm copper emission line.

The next step involves dividing the 324 copper emission line "intensity" (e.g., area) by the 336 silver emission line "intensity" (e.g., area) to arrive at a normalized ratio value.

Finally, the intensity calibration curve for copper is used to determine the concentration of the constituent element copper in the fluid sample as a function of the copper area/silver area ratio value. The concentration of copper, as well as other constituent elements, are then provided to an expert system for diagnosis.

EXPERT SYSTEM

Apparatus 10 acquires analytical data from various measurement subsystems, under the control of controller 28. After processing as described above, the constituent concentration data, for example concentrations as expressed in parts per million (PPM) of various wear metals, percentage water, and the like, are then provided to an expert software system. The expert system, in connection with a set of rules ("Rules"), and a database, generates diagnostic statements regarding the assessment of the condition of the fluid (e.g., oil) and/or the operating equipment associated therewith.

The expert system executes on controller 28 and is operative to evaluate the plurality of Rules in response to the constituent concentration parameters as well as other data and produces a plurality of output signals. The expert system then determines a condition or state of the lubricating oil or functional fluid and/or the equipment (or component thereof), from which the fluid sample was drawn as a function of the output signals.

The Rules comprise a set of logical statements: IF/THEN/ELSE, AND, and OR. Evaluating a logical statements will return a true or false result. The logical statements are evaluated based on data that are input into the computer controller 28 by the end user, predetermined operating data, as well as the test result data generated by FTIR assembly 24 and OES assembly 26.

The expert system includes memory for storing information regarding tested fluid samples. For each sample, a corresponding data structure stored in memory may contain the following pieces of information associated therewith: system type (i.e., the type of equipment selected from an equipment list by the end user, such as gasoline engine, diesel engine, and the like); make/model, engine size, time on unit (hours or miles), time on oil (i.e., since last change), oil sump capacity, as well as a variety of other pieces of information. See, for example, FIG. 17 showing an output report 174 as well as a variety of input fields (identification, oil brand, oil type, and the like).

Predetermined operating data include a database of numerical concentration levels of particular constituent elements that trigger a rating flag associated with each element for which apparatus 10 has been programmed to detect. The flag may assume several states, namely, following: Normal= "N", Low Normal="LN", Abnormal="A", High Normal= "HN", Excessive="E", or Severe "S". This rating flag, as shown in FIG. 17, if applicable, may be printed out next to the wear metal.

Figure 16:
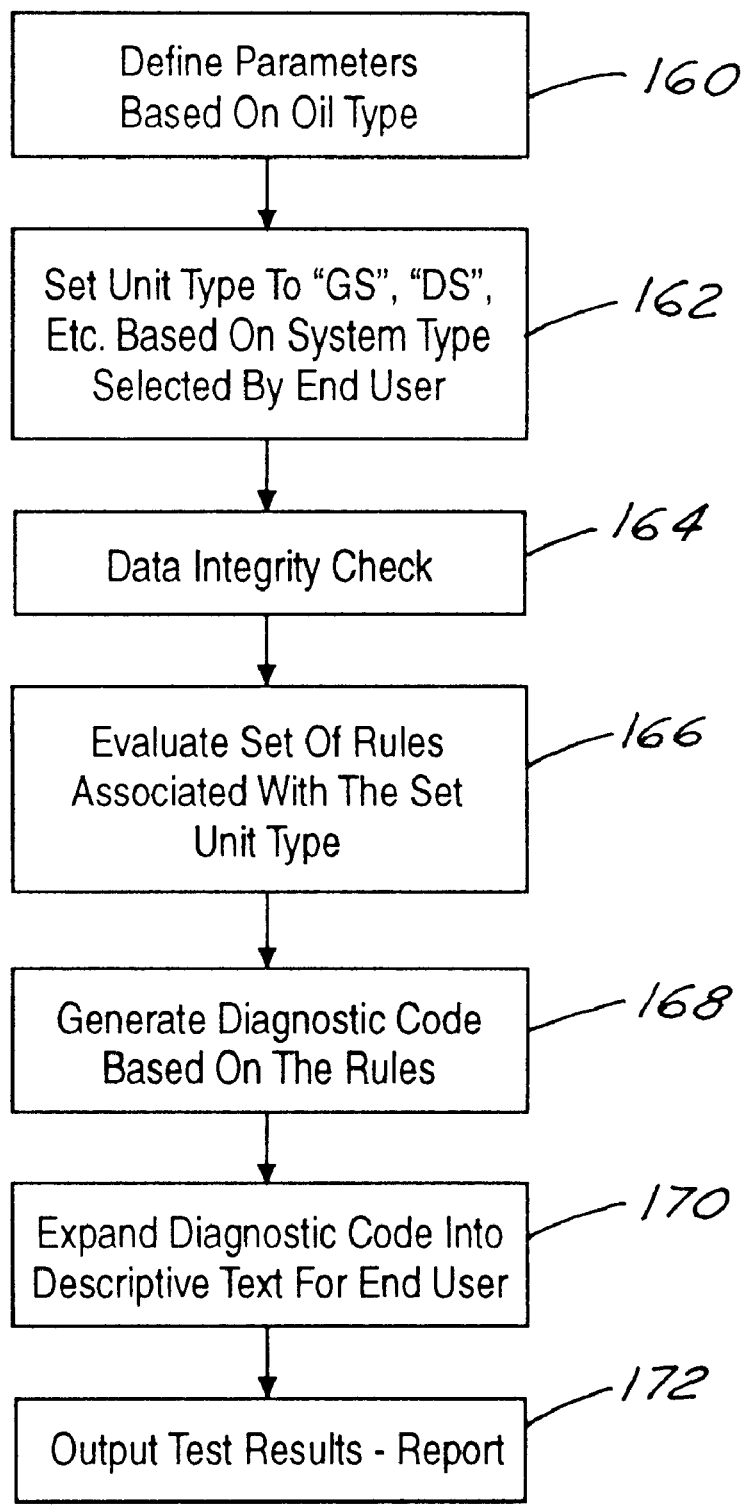
FIG. 16 is a simplified flow chart diagram of the operation of an expert system portion of the apparatus of FIG. 1.

Referring now to FIG. 16, the basic operation of the expert software system will now be set forth in detail.

In step 160, the program ("expert system") executing on controller 28 defines parameters for each oil type that the end user selects from the oil type pick list. For example, for a particular oil type, high and low limits for viscosity @100c will be set.

In step 162, the unit type parameter is set to "GS", "MDS", "MGS", "MGR", "DS", "RRC", "RRD", "MT", "AT"etc. based on the system type that was selected by the end user from the equipment selection list. For example only, and without limitation, "GS" stands for gasoline engine; "MDS" stands for marine diesel; "MGS" stands for marine gasoline; "MGR" stands for marine gear; "DS" stands for diesel engine; "RRC" stands for railroad compressor; "RRD" stands for railroad diesel; "MT" stands for manual transmission; and, "AT" stands for automatic transmission.

In step 164, the program performs an integrity check of the FTIR test results to insure the quality of the diagnostic process. For example, if the value of soot, $H_2O$ or SYNTH are above a certain cutoff point, then the remainder of the FTIR properties will be effectively ignored (and the printout will replace actual measurements with an "*").

In step 166, the expert program evaluates a set of rules associated with the set unit type. The evaluation step evaluates only those rules that are specifically designed for the selected unit type, as defined in step 162 above. For example, if the customer selects gasoline engine as the type of sample that needs to be tested, then step 162 will set unit type to "GS", and thus all rules have the prefix "GS" will be evaluated, in light of measurement test results.

In step 168, the expert system generates a diagnostic code based on the evaluation of the rules. In a constructed embodiment, the diagnostic code is a two alphanumeric character code, which is an internal shorthand for a simple, easy to understand block of text provided to the end user on the screen and/or printed report.

In step 170, the diagnostic code is expanded into descriptive text for the end user, appropriate formatting is done (e.g., replace all negative numbers with appropriate default values, and all values that exceed a predetermined limit with a greater than sign ">" next to a predetermined number, and the like).

In step 172, the test results are output, an example of which is shown in FIG. 17 as report 174.

The Expert System also recognizes that factors other than equipment wear may vary wear metal concentrations. For example, a Mileage Adjustment Factor ("MAF") formula is designed to adjust the alarm limits for the Wear Metal Elements based on the Time On Oil. The longer the oil stays in the engine the more wear particles will accumulate.

The Rules, as noted above, are logical statements that are evaluated during analysis, and, in a constructed embodiment, may take the form as follows:

Rules
Diagnostic Code
Condition1
Operand
Condition2
.
.
.
etc.
Statement if the combination of all conditions are True Each Rule set (e.g. "RULEDS") comprises a plurality of rules to be evaluated. Below are examples of various rules included in rule set designated "RULEDS" (i.e., diesel).

| RuleDS |
|---|

```
************************************************************
Rules that contain different combination conditions for "OES"    *
************************************************************
```
1. 'EVERYTHING IS NORMAL
EA, SP, 18
IF Not BKOH And allNormal("Al,Cr,Cu,Fe,Pb,Sn")
AND
allNormal("Si,K,Na,H2O,Fuel,Soot,GLY,V100C,Oxi")
AND
UCase$(CurOilWeight) <> "UNKNOWN"
ALL ENGINE WEAR RATES NORMAL. ANALYSIS INDICATES PROPER
PERFORMANCE OF THE LUBRICANT AND UNIT. SAMPLE APPEARS FREE OF
EXTERNAL CONTAMINATION.
2. FE-ABN AND CR-NOR
EG
If getGrade("Fe") <> N And Not (BKOH Or getDiagCode("ED") Or getDiagCode("EP") Or
getDiagCode("ER") Or getDiagCode("ES") Or getDiagCode("ET") Or getDiagCode("EZ"))
CYLINDER, CRANK OR CAM SHAFT WEAR INDICATED.
```
************************************************************
These are Make Specific Rules                                    *
************************************************************
```
1. AL-A & (Cr + Fe) N-N or Engine Make is not Detroit 53, 71,92
EH
If getGrade("Al") <> N And Not(BKOH Or checkDetroit Or getDiagCode("ER") Or
getDiagCode("EP") Or getDiagCode("EZ") Or getDiagCode("ES"))
PISTON WEAR INDICATED.
2. 'SI-ABN & [(AL,CR,FE) Non Detroit Eng. OR (SN,CR,FE) Detroit Eng. Model
53,71,92] N-N
CD, RQ
If Not (BKOH Or getDiagCode("BM") Or getDiagCode("DG")) And getGrade("Si") = A And
anyNotNormal("Al,Cr,Fe")
AND
(getGrade("Si") = A And anyNotNormal("Al,Cr,Fe"))
DIRT PRESENT. CHECK FILTER AND AIR INDUCTION SYSTEM.
3. [(SN+CR+FE+(CU,PB,AL) N-N]    FOR    DETROIT    53,71,92    OR
[(AL+CR+FE+(CU,PB,SN) N-N]
ER, AA, RZ
If checkDetroit And (allNotNormal("Sn,Cr,Fe") And anyNotNormal("Cu,Pb,Al")) And Not
BKOH
OR
If Not (BKOH Or checkDetroit) And (allNotNormal("Al,Cr,Fe") And
anyNotNormal("Cu,Pb,Sn"))
AND
If (anyNotNormal("Al,Cr,Fe"))
AND
If getDiagCode ("ER") Or getDiagCode("TN") Or getDiagCode("EB") Or
getDiagCode("ES") Or getDiagCode("EZ") And Not(getDiagCode("CG") Or
getDiagCode("T4"))
PISTON, RING, CYLINDER AND BEARING WEAR INDICATED. CHECK FOR
POWER LOSS, BLOW-BY, SMOKING, OIL CONSUMPTION, ETC. CHECK FOR
OIL PRESSURE DROP AND ABNORMAL NOISE.
```
************************************************************
Rules that contain different combination conditions for the "FTIR"  *
************************************************************
```
1. 'HIGH H2O-SEVERE
YK, SC
If getGrade("H2O") = S And Not getDiagCode("CS")
AND
If getRawConc("H2O") > 0.5 And Not getDiagCode("CS")
HEAVY CONCENTRATION OF WATER PRESENT. CHECK FOR SOURCE OF
WATER ENTRY.
```
************************************************************
Rules for High Wear Metals Elements in Break-In/Overhaul         *
************************************************************
```
1. 'AL-ABN (BKOH)
JA
    If (BKOH And getGrade("Al") = A And Not(getDiagCode("EV") Or (CurVehicleTime =
    CurOilTime))) Then
ALUMINUM LEVEL HIGHER THAN TYPICAL FOR BREAK-IN/OVERHAUL PERIOD.
```
************************************************************
QC RULES                                                         *
************************************************************
```
1. 'REPLACE V100C W/NA IF SOOT > 1.8
48
If getRawConc("Soot") > 1.8
setError "V100C"
* SOOT LEVEL LIMITS THE ACCURACY OF THE ANALYSIS DATA.

-continued

RuleDS

2. 'REPLACE V100C W/NA IF WATER > 3.0
49
If getRawConc("H2O") > 3.0
setError "V100C"
* HIGH WATER LEVEL LIMITS LIMITS THE ACCURACY OF THE ANALYSIS DATA.

It should be appreciated from the foregoing that evaluation of the Rules results in an intelligent inference regarding the status of the equipment from which the fluid sample is drawn. Based on the inference, an appropriate message is provided for example: "ALUMINUM LEVEL HIGHER THAN TYPICAL FOR BREAK-IN/OVERHAUL PERIOD."

Apparatus 10, under full computer control, performs all data preprocessing, and data extraction to obtain relevant analysis data pertinent to the specific analyses that are being performed. Calibrations are based on built-in calibration information. The final sample data are then presented to an expert system, which is used for the generation of diagnostic statements for the assessment of the condition of the fluid (oil) and/or the operating equipment. The final results are presented on a flat panel display for operator review, and are also available for hard copy generation, archive storage and/or communication via modem or to a local network via an Ethernet connection.

While the present invention was illustrated and described with respect to a preferred embodiment, such description is exemplary only and not limiting in nature. Other aspects, objects, and advantages of this invention may be obtained from the study of the drawings, and the disclosure. It is well understood by those skilled in the art that various changes and modifications can be made in the invention without departing from the spirit and scope thereof, which is limited only by the appended claims. For example, the selection of measurement devices are not limited to arc emission spectrometers, FTIRs and viscometers. An apparatus in accordance with the invention may also include, where appropriate, other forms of absorption spectrometers, such as UV-visible spectrometers, for composition and color measurements, other forms of emission spectrometers, such as fluorescence and Raman spectrometers, electrical property measurements, such as resistivity, capacitance and conductivity for rudimentary condition monitoring, laser-based optical measurements, such as composition monitoring and light scattering devices, and other physical measurement devices providing diagnostic information that can be automated, and can be interpreted meaningfully by a computer-based expert system.

We claim:

1. A method of normalizing an intensity of and regularizing a sample spectrum of a fluid sample generated by a spectrometer having a pair of electrodes, the method comprising the steps of normalizing the intensity by:
   selecting a background spectral feature from a plurality of spectral features of a background spectrum that is indicative at least in part of the composition of the electrodes wherein the background spectral feature has an intensity variation characteristic; and
   transforming the sample spectrum with respect to intensity in accordance with an intensity of said selected background spectral feature as indicated in the sample spectrum;

the method comprising regularizing the intensity by:
   (A) defining a background spectrum having a plurality of spectral features indicative at least in part of the composition of the electrodes;
   (B) selecting at least a first background spectral feature from said plurality of spectral features wherein the first background spectral feature has a predetermined wavelength value associated therewith;
   (C) determining a measured wavelength value of the at least first background spectral feature in the sample spectrum; and
   (D) translating the sample spectrum with respect to wavelength in accordance with said predetermined wavelength value, said measured wavelength value, and a predetermined translation strategy.

2. The method of claim 1 wherein the sample spectrum comprises an array of values representative of wavelengths and spectral intensities associated therewith over a spectral range, wherein said plurality of spectral features are defined by corresponding emission lines, and wherein step (B) is performed by the substep of:
   selecting a plurality of emission lines from the background spectrum wherein each selected emission line has a respective predetermined wavelength value associated therewith.

3. The method of claim 2 wherein step (C) is performed by the substeps of:
   identifying the plurality of selected background emission lines in the array of values; and,
   determining a respective measured wavelength value of the identified emission lines in the array.

4. The method of claim 3 wherein step (D) is performed by the substeps of:
   determining a respective wavelength offset between the predetermined wavelength values and the measured wavelength values;
   converting the wavelength offsets into a composite wavelength offset for the sample spectrum;
   determining a pixel shift number as a function of the composite wavelength offset; and,
   shifting the spectral intensities of the array of values by the pixel shift number to thereby regularize the sample spectrum with respect to wavelength.

5. The method of claim 1 wherein the fluid sample comprises one of used lubricating oil and used functional fluid, and step (A) includes the substeps of:
   exciting a new sample of said one of lubricating oil and functional fluid corresponding in type and grade to the used sample to spectroemissive levels to thereby generate radiation;
   acquiring a background spectrum responsive to the radiation; and,
   storing the background spectrum for subsequent use.

6. A method of normalizing an intensity of a sample spectrum of a fluid sample by a spectrometer having a pair of electrodes, the method comprising the steps of:

(A) selecting a background spectral feature from a plurality of spectral features of a background spectrum that is indicative at least in part of the composition of the electrodes wherein the background spectral feature has an intensity variation characteristic; and (B) transforming the sample spectrum with respect to intensity in accordance with an intensity of said selected background spectral feature as indicated in the Sample spectrum;

the method further comprising the step of regularizing the sample spectrum.

7. The method of claim 6 wherein the step of regularizing the sample spectrum comprises translating the sample spectrum with respect to wavelength in accordance with a first background spectral feature having a known wavelength selected from a background spectrum having a plurality of spectral features indicative at least in part of the composition of the electrodes.

8. The method of claim 7 wherein the sample spectrum is one of a lubricating oil sample and a functional fluid sample having one or more constituent elements, further comprising the steps of:

determining an intensity of a second background spectral feature having an intensity variation characteristic;

determining an intensity of a characteristic emission line associated with at least one of the constituent elements;

transforming the constituent element intensity into a concentration parameter using (i) the intensity of the second background spectral feature in the sample spectrum, (ii) the intensity of the constituent emission line, and (iii) predetermined data.

9. The method of claim 6 further comprising the step of subtracting a reference spectrum from said sample spectrum.

10. The method of claim 9 further comprising the step of adjusting intensity of said reference spectrum before the step of subtracting.

11. The method of claim 10 wherein the step of adjusting is performed with reference to a spectral space where there are no significant spectral features.

12. The method of claim 9 wherein said step of subtracting is performed on a point-by-point basis.

13. A method of normalizing an intensity of a sample spectrum of a fluid sample by a spectrometer having a pair of electrodes, the method comprising the steps of:

(A) selecting a background spectral feature from a plurality of spectral features of a background spectrum that is indicative at least in part of the composition of the electrodes wherein the background spectral feature has an intensity variation characteristic; and (B) transforming the sample spectrum with respect to intensity in accordance with an intensity of said selected background spectral feature as indicated in the sample spectrum;

wherein the fluid sample contains constituents, and wherein step (A) is performed by the substeps of:

identifying an emission line associated with at least one constituent;

selecting a first set of spectral features from the plurality of spectral features of the background spectrum;

obtaining a predetermined number of spectra of the fluid sample using the pair of electrodes;

determining a first intensity variation of said identified emission line over said predetermined number of spectra;

determining, for each spectral feature in said first set, a respective second intensity variation over said predetermined number of spectra;

selecting spectral features from said first set that have a respective second intensity variation that is less than said first intensity variation to thereby form a second set of spectral features;

selecting one of the spectral features from said second set based on predetermined criteria.

14. The method of claim 13 wherein determining a respective second intensity variation step comprises the substeps of:

dividing, for each one of said predetermined number of spectra, the intensity of the identified emission line of the constituent by the intensity of the respective background spectral feature in the first set to thereby produce ratio values; and, calculating said second intensity variation using said ratio values.

15. The method of claim 13 wherein step (B) includes the substeps of:

measuring the intensity of the background spectral feature in the sample spectrum; and, ratioing at least a portion of the intensity of the sample spectrum by the measured intensity of the background spectral feature.

16. The method of claim 15 wherein the electrodes comprise silver material and the background spectral feature comprises a 336 nm silver emission line, and the measured intensity comprises area under a curve associated with the 336 nm silver line.

17. A method of analyzing a sample spectrum of one of lubricating oil sample and a functional fluid sample having one or more constituent elements wherein the sample spectrum is generated by a spectrometer having a pair of electrodes, the method comprising the steps of:

(A) translating the sample spectrum with respect to wavelength in accordance with a first background spectral feature having a known wavelength selected from a background spectrum having a plurality of spectral features indicative at least in part of the composition of the electrodes;

(B) determining an intensity of a second background spectral feature having an intensity variation characteristic;

(C) determining an intensity of a characteristic emission line associated with at least one of the constituent elements;

(D) transforming the constituent element intensity into a concentration parameter using (i) the intensity of the second background spectral feature in the sample spectrum, (ii) the intensity of the constituent emission line, and (iii) predetermined data.

18. The method of claim 17 wherein step (D) further includes the substep of:

subtracting a reference spectrum from the sample spectrum.

19. The method of claim 17 wherein the sample spectrum comprises an n-row array of values representative of wavelengths and spectral intensities associated therewith over a spectral range where n corresponds to a number of pixels of an imaging device in the spectrometer, and wherein step (A) is performed by the substeps of:

selecting multiple emission lines from the plurality of spectral features of the background spectrum wherein each emission line has a predetermined known, wavelength value;

determining a respective measured wavelength value for the multiple emission lines in the array of values;

determining a respective wavelength offset between the predetermined known wavelength values and the measured wavelength values, for each selected emission line;

determining a pixel shift number as a function of the wavelength offsets; and, shifting the spectral intensifies in the array by the pixel shift number.

20. The method of claim 19 further including the steps of:

evaluating a plurality of rules in response to the constituent concentration parameter and producing a plurality of output signals; and, determining a condition of a component of equipment from which the sample was drawn as a function of said output signals.

* * * * *